US012728023B2

(12) United States Patent
Sebkhi et al.

(10) Patent No.: US 12,728,023 B2
(45) Date of Patent: Sep. 8, 2026

(54) MOTION TRACKING USING MAGNETIC-LOCALIZATION INERTIAL MEASUREMENT UNIT AND ORIENTATION COMPENSATION

(71) Applicant: GEORGIA TECH RESEARCH CORPORATION, Atlanta, GA (US)

(72) Inventors: Nordine Sebkhi, Atlanta, GA (US); Arpan Bhavsar, Atlanta, GA (US); Omer Inan, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 177 days.

(21) Appl. No.: 18/270,956

(22) PCT Filed: Jan. 4, 2022

(86) PCT No.: PCT/US2022/011066
§ 371 (c)(1),
(2) Date: Jul. 5, 2023

(87) PCT Pub. No.: WO2022/147516
PCT Pub. Date: Jul. 7, 2022

(65) Prior Publication Data

US 2024/0082032 A1 Mar. 14, 2024

Related U.S. Application Data

(60) Provisional application No. 63/133,543, filed on Jan. 4, 2021.

(51) Int. Cl.
*A61F 4/00* (2006.01)
*A61G 5/04* (2013.01)
(Continued)

(52) U.S. Cl.
CPC .................. *A61F 4/00* (2013.01); *A61G 5/04* (2013.01); *B25J 9/1694* (2013.01); *G01C 21/16* (2013.01);
(Continued)

(58) Field of Classification Search
CPC . A61F 4/00; A61G 5/04; B25J 9/1694; G01C 21/16; G06F 3/012; G06N 3/0499;
(Continued)

(56) References Cited

U.S. PATENT DOCUMENTS 5,744,953 A * 4/1998 Hansen .................. G06F 3/011
5,930,741 A * 7/1999 Kramer .................. G06F 3/011
(Continued)

OTHER PUBLICATIONS

Sebkhi N, Bhavsar A, Anderson DV, Wang J, Inan OT. Inertial Measurements for Tongue Motion Tracking Based on Magnetic Localization with Orientation Compensation. IEEE Sens J. Mar. 15, 2021;21(6):7964-7971. doi: 10.1109/jsen.2020.3046469. Epub Dec. 22, 2020. PMID: 33746627; PMCID: PMC7978385. (Year: 2020).*
(Continued)

*Primary Examiner* — Ellis B. Ramirez
(74) *Attorney, Agent, or Firm* — Meunier Carlin & Curfman LLC

(57) ABSTRACT

An exemplary motion tracking and/or localization system is disclosed that can provide a non-line-of-sight motion tracking with millimetric accuracy for a tracer moving in close proximity to a magnetic source. In some embodiments, the tracking and/or localization system includes an inertial measurement unit (IMU) configured as a tracer that can move in a local magnetic field generated by multiple local magnetic sources.

22 Claims, 10 Drawing Sheets

(51) Int. Cl.

| | |
|---|---|
| ***B25J 9/16*** | (2006.01) |
| ***G01C 21/16*** | (2006.01) |
| ***G06F 3/01*** | (2006.01) |
| ***G06N 3/0499*** | (2023.01) |
| ***G06N 3/08*** | (2023.01) |

(52) U.S. Cl.
CPC ........... *G06F 3/012* (2013.01); *G06N 3/0499* (2023.01); *G06N 3/08* (2013.01)

(58) Field of Classification Search
CPC ......... G06N 3/08; A61B 5/1126; A61B 5/682; A61B 5/6802; A61B 5/1114; A61B 5/7267; A61B 2562/0219; A61B 2562/0223; G01R 33/0029; G01R 33/0094; G01R 33/0017; G01R 33/038
USPC ............ 700/258; 702/94; 600/595; 341/155; 340/539.12, 539.22; 73/504.03
See application file for complete search history.

(56) References Cited

U.S. PATENT DOCUMENTS

| | | | | |
|---|---|---|---|---|
| 8,242,880 | B2 * | 8/2012 | Ghovanloo | A61F 4/00 |
| 8,758,275 | B2 * | 6/2014 | Kourogi | G01C 21/28 |
| 2002/0103610 | A1 | 8/2002 | Bachmann et al. | |
| 2007/0032748 | A1 * | 2/2007 | McNeil | A61B 5/1121 |
| 2007/0270722 | A1 | 11/2007 | Loeb et al. | |
| 2009/0007661 | A1 | 1/2009 | Nasiri et al. | |
| 2012/0283856 | A1 * | 11/2012 | Caritu | G01P 13/02 |
| 2013/0090831 | A1 | 4/2013 | Kwon et al. | |
| 2013/0090931 | A1 * | 4/2013 | Ghovanloo | A61F 4/00 |
| 2014/0081180 | A1 * | 3/2014 | Ghajar | A61F 5/055 |
| 2016/0047675 | A1 * | 2/2016 | Tanenhaus | G01C 25/005 |
| 2020/0093571 | A1 * | 3/2020 | Shanjani | A61C 7/002 |
| 2020/0405231 | A1 * | 12/2020 | Mohrman | A61B 5/7246 |
| 2022/0142713 | A1 * | 5/2022 | Oren | A61B 5/287 |

OTHER PUBLICATIONS

N. Sebkhi et al., “A Deep Neural Network-Based Permanent Magnet Localization for Tongue Tracking,” in IEEE Sensors Journal, vol. 19, No. 20, pp. 9324-9331, Oct. 15, 15, 2019, doi: 10.1109/JSEN.2019.2923585. (Year: 2019).*

International Search Report and Written Opinion received in PCT/US2022/011066 mailed Mar. 24, 2022.

Torres et al. “Motion tracking algorithms for inertial measurement.” Proceedings of the ICST 2nd international conference on Body area networks. 2007. Jun. 11, 2007 (Jun. 11, 2007) Retrieved on Mar. 8, 2022 (Mar. 8, 2022) from <https://eudl.eu/pdf/10.4108/bodynets.2007.170> entire document.

Filippeschi et al. “Survey of motion tracking methods based on inertial sensors: A focus on upper limb human motion.” Sensors 17.6 (2017): 1257. Jun. 1, 2017 (Jun. 1, 2017) Retrieved on Feb. 27, 2022 (Feb. 27, 2022) from <https://www.mdpi.com/1424-8220/17/6/1257> entire document.

Sebkhi et al. “Inertial Measurements for Tongue Motion Tracking Based on Magnetic Localization With Orientation Compensation.” IEEE Sensors Journal 21.6 (2021): 7964-7971. Retrieved on Mar. 7, 2022 (Mar. 7, 2022) from <https://www.researchgate.neVpublication/347849924> entire document.

Extended European Search Report received in Application No. 22734827.3, mailed Oct. 11, 2024.

Shen Hui-Min et al: “Full-pose estimation using inertial and magnetic sensor fusion in structurized magnetic field for hand motion tracking”, Measurement, Institute of Measurement and Control. London, GB, vol. 170, EPUB Nov. 8, 2020 (Nov. 8, 2020), XP086438608, ISSN: 0263-2241, DOI: 10.1016/J.Measurement.2020.108697.

* cited by examiner

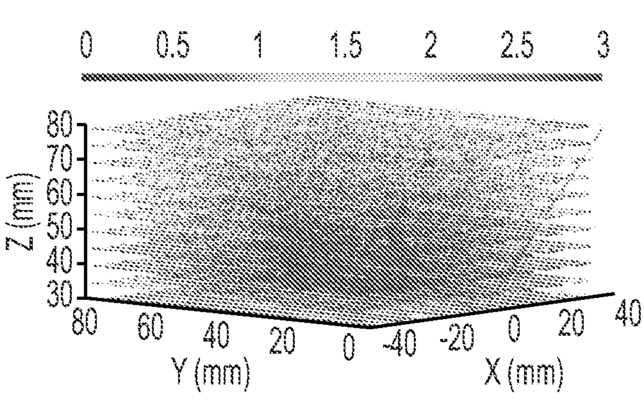
FIG. 4A
POSITIONAL ERROR(mm)
TRAINING VALIDATION TESTING
FIG. 4D
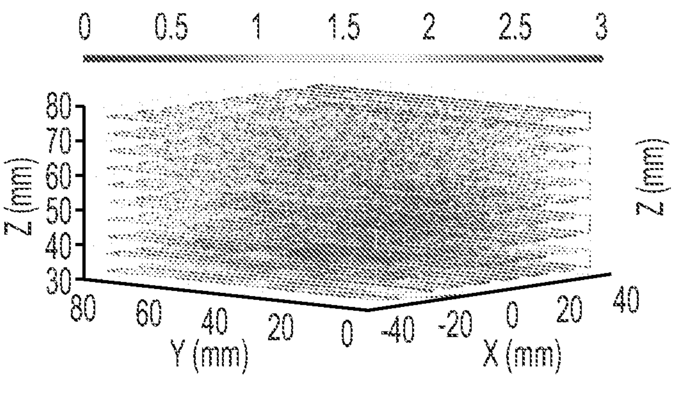
FIG. 4B
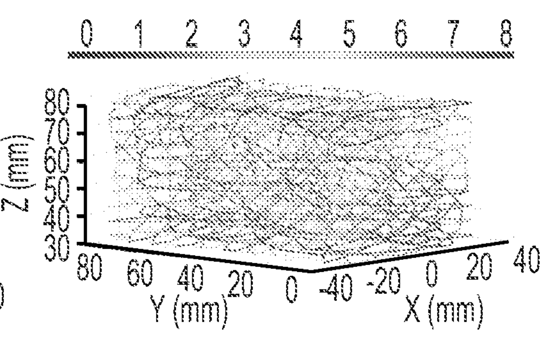
FIG. 4E
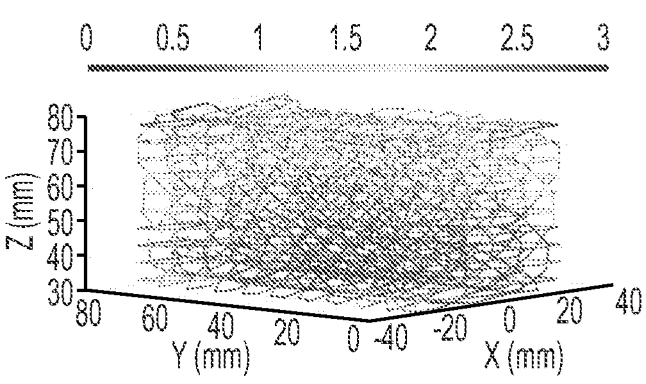
FIG. 4C
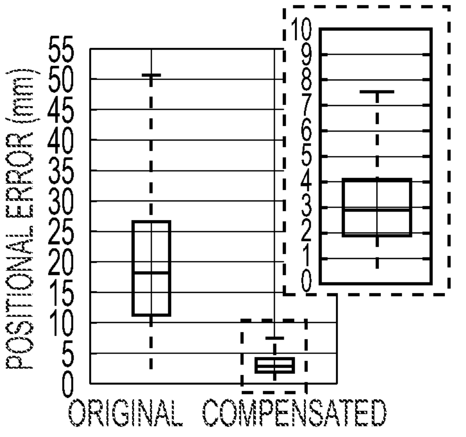
FIG. 4F

MOTION TRACKING USING MAGNETIC-LOCALIZATION INERTIAL MEASUREMENT UNIT AND ORIENTATION COMPENSATION

RELATED APPLICATION

This application is a U.S. National Stage application filed under 35 U.S.C. § 371 of PCT/US2022/011066, filed Jan. 4, 2022, which claims priority to, and the benefit of, U.S. Provisional Application No. 63,133,543, filed Jan. 4, 2021, entitled "Motion Tracking Using Magnetic-Localization Inertial Measurement Unit and Orientation Compensation," each of which is incorporated by reference herein in its entirety.

TECHNICAL FIELD

The present disclosure generally relates to methods and systems for performing motion tracking using localization, specifically, magnetic-based localization with orientation compensation from wearable sensors. The localization may be used for monitoring, tracking, or controls of medical equipment, speech rehabilitation, or entertainment systems.

BACKGROUND

Motion tracking technologies are employed in applications for medical/assisted technology, robotics, sports, virtual/augmented reality, and entertainment. Chief among them is the tracking of body motion for medical applications, which, for example, is included as part of assistive technologies to assist in the rehabilitation of physical disabilities, or as an alternative control used by people with quadriplegia. Motion tracking of the tongue or other facial features (e.g., cheek, jaw, eyebrow) is desired in many such applications but remains impractical due to the challenge associated with the localization of the sensor on the tongue or face.

Permanent magnet localization (PML) has the potential to overcome many of the shortcomings of the current tracking technologies in providing a small unintrusive tracer that can provide continuous tracking in a whole 3D space. Prior PML systems can not distinguish between multiple magnetic sources and employed multiple magnetometers placed around the magnetic sources (e.g., the head) to measure a single magnetic source.

There is a technical benefit to improving the operation of motion tracking technologies, including permanent magnet localization.

SUMMARY

An exemplary motion tracking and/or localization system is disclosed that can provide a non-line-of-sight motion tracking with millimetric accuracy for a tracer moving in close proximity to a magnetic source (in the range of centimeters to a few decimeters). In some embodiments, the tracking and/or localization system includes an inertial measurement unit (IMU) configured as a tracer that can move in a local magnetic field generated by one or multiple local magnetic sources (e.g., an array of permanent magnets or an electromagnet). In some embodiments, the IMU may include a magnetometer, accelerometer, and gyroscope that are co-located on a single tracer or integrated into a single package. The exemplary motion tracking and/or localization is configured to employ a reverse permanent magnetic localization operation in which a constant and local magnetic field is generated by multiple magnetic sources in the effective sensing environment, and one or more magnetic sensor(s) (e.g., magnetometer), preferably one, are allowed to move within that local field to provide localization measurement at the magnetic sensor(s). The magnetic sensor readings are adjusted to remove background magnetic field readings and provided to a trained neural network or trained machine learning operation to output a localization-associated measurement value (e.g., the localized position or relative position of the magnetic sensor). While one magnetic sensor would be sufficient to provide millimetric measurement for most applications, the algorithm can operate using multiple magnetic sensor readings. In such embodiments, the exemplary motion tracking and/or localization system can employ multiple magnetic sensors, which may be suitable, e.g., in applications where higher fidelity measurements are warranted. The determined localization-associated measurement value can be provided to a controller, e.g., for a control operation, e.g., as a motor control signal or command to a motored wheelchair or in a human-machine interface operation, e.g., with a computing device, or in a computing virtualized environment. In some embodiments, the local magnetic source may be a set of permanent magnets or electromagnets.

The magnetic sensor can be configured in a small form factor (e.g., 6 mm×6 mm×0.8 $mm^3$) to be place comfortably and inconspicuously on the body while the multiple magnetic sources can be disposed at the neck (e.g., in a collar), at the back of the ear, over the head (e.g., in a cap, head band, or skin patch), in eyewear, or inside the mouth (e.g., behind the teeth or on retainers) so as to be away from the user's face and can be inconspicuously hidden from view.

In some embodiments, the exemplary motion tracking and/or localization system can be configured to employ accelerometer and/or gyroscope readings, e.g., of the IMU, to estimate the orientation of the tracer and to use that orientation information to calibrate or re-orient the magnetic field readings of the IMU's magnetic sensor to a reference frame. In such embodiments, the orientation-compensated magnetic field is then used in a localization algorithm, e.g., a trained neural network or trained machine learning operation, to estimate the relative 3D position of the tracer with respect to the magnetic source. It is observed that using tracer rotation data, e.g., from an accelerometer and/or gyroscope readings, in the training of a tracer motion algorithm can improve the performance of a trained neural network or trained machine learning model (e.g., by reducing the complexities of the magnetic features when the sensor is rotated).

In one configuration, the exemplary motion tracking and/or localization system was configured with a mouth sensing area of about 8 cm×8 cm×5 cm volume having a positional error of about 1 mm (median) and 1.5 mm (third quartile, Q3). The same system was observed to have an error of about 2.9 mm (median) and about 4.2 mm (Q3) when evaluation for rotation (±50°) along with both pitch and roll. In another configuration, the exemplary motion tracking and/or localization system was configured with a mouth sensing area of about 10 cm×12 cm×10 cm having a positional error of 2 mm (third quartile, Q3).

The exemplary motion tracking and/or localization system provides an alternative approach to existing motion tracking systems, especially as a practical, affordable, and wearable motion tracking system (e.g., tongue tracking system) to be used in various applications. The exemplary motion tracking and/or localization system can also be used as the front-end system for a silent speech interface, a treatment tool in speech therapy, and an alternative control paradigm for people with quadriplegia, among other applications as for example described herein.

In an aspect, a method is disclosed for tracking motion of a body part, the method comprising receiving a set of one or more motion-associated signals from one or more wearable sensors disposed on the body part, wherein the one or more wearable sensors include a first wearable sensor that is one of a motion sensor, a position sensor, or an inertial measurement sensor; receiving a set of one or more magnetic measurement associated signals from one or more magnetic sensors disposed on the body part, wherein the one or more magnetic sensors are fixed in relation to the first wearable sensor, and wherein the one or more magnetic sensors are placed in proximity to one or more local magnetic field sources disposed on the body; and determining, by a processor, a localization-associated measurement value (e.g., x, y, z positions) using the magnetic measurement associated signals and the one or more motion-associated signals, wherein the localization-associated measurement value has been determined from the magnetic measurement associated signals adjusted by the one or more motion-associated signals.

In some embodiments, the method further includes determining, by the processor, a motion-associated measurement value, wherein the motion-associated measurement value has been determined from the motion-associated signals and adjusted for measurement drift based on the localization-associated measurement value.

In some embodiments, the one or more wearable sensors further include a second wearable sensor that is one of the motion sensor, the position sensor, or the inertial measurement sensor, wherein the second wearable sensor is a different type from the first wearable sensor.

In some embodiments, the first wearable sensor is an accelerometer, and wherein the second wearable sensor is a gyroscope-based sensor.

In some embodiments, the adjustment for the measurement drift based on the one or more magnetic measurement-associated signals includes compensation for magnetic localization.

In some embodiments, the magnetic measurement associated signals is adjusted by orientation or angle estimations derived from an accelerometer and/or gyroscopic reading.

In some embodiments, the localization-associated measurement value comprises a first position value, a second position value, and a third position value.

In some embodiments, the motion-associated measurement value is adjusted by the localization-associated measurement value via a weighted average operation over time.

In some embodiments, the motion-associated measurement value is adjusted by the localization-associated measurement value via a dynamic averaging operation.

In some embodiments, the localization-associated measurement value is determined using a trained neural network.

In some embodiments, the neural network is trained using magnetic measurement associated signals acquired by a test rig configured to provide one or more axis position data and one or more orientation data.

In some embodiments, the localization-associated measurement value is determined using a trained machine learning algorithm (e.g., LSTM, decision tree) or a transfer function derived from dynamic system analysis.

In some embodiments, the machine learning algorithm is trained using magnetic measurement associated signals acquired by a test rig configured to provide one or more position data and one or more orientation data.

In some embodiments, the method further includes outputting a motor control signal or command to a wheelchair using the motion-associated measurement value in a human-machine interface operation.

In some embodiments, the localization-associated measurement value and/or the motion-associated measurement value is used in a human-machine interface operation for a robotic control or motion control application (e.g., to steer or drive a motorized wheelchair).

In some embodiments, the localization-associated measurement value and/or the motion-associated measurement value is used in a human-machine interface operation for a computer application (e.g., video games).

In some embodiments, the localization-associated measurement value and/or the motion-associated measurement value is used in a human-machine interface operation to direct robotic control or motion control based on sensed location or motion of the tongue, face, lip, head.

In some embodiments, the localization-associated measurement value and/or the motion-associated measurement value is used to track tongue motion for speech therapy assessment or treatment.

In some embodiments, the one or more local magnetic field sources are disposed at the neck (e.g., in a collar), at the back of the ear, over the head (e.g., in a cap, head band, or skin patch), in eyewear, or inside the mouth (e.g., behind the teeth or on retainers).

In another aspect, a system is disclosed comprising: a plurality of wearable sensors, including a first wearable sensor that is one of a motion sensor, a position sensor, or an inertial measurement sensor; one or more local magnetic field source to operate with one or more magnetic sensors; the one or more magnetic sensors, wherein the one or more magnetic sensors are fixed in relation to the first wearable sensor, and wherein the one or more magnetic sensors is placed in proximity to the one or more local magnetic field source; and a processing unit coupled (wired or wirelessly) to the plurality of wearable sensors through one or more sensor interface circuitries configured to convert signals received from the plurality of wearable sensors to motion-associated measurement values, the processing unit comprising a processor and memory, the memory having instructions stored thereon, wherein the instructions when executed by the processor causes the processor to: receive a set of one or more motion-associated signals from the one or more wearable sensors; receive a set of one or more magnetic measurement associated signals from the one or more magnetic sensors; and determine a localization-associated measurement value using the magnetic measurement associated signals and the one or more motion-associated signals, wherein the localization-associated measurement value has been determined from the magnetic measurement associated signals adjusted by the one or more motion-associated signals.

In some embodiments, the system includes a housing configured as eyewear or an earpiece, wherein the housing includes a compartment for the processing unit.

In some embodiments, the system further includes a second set of wearable sensors configured to be mounted at a second body location, wherein the second set of wearable sensors are configured to output one or more reference signals (e.g., for body motion), and wherein the one or more reference signals are used to adjust measurements (e.g., remove motion artifacts) of the localization-associated measurement value or a motion-associated measurement value determined at a second body position.

In some embodiments, the plurality of wearable sensors and the one or more magnetic sensors are co-located on a substrate configured to be positioned on a portion of a tongue.

In some embodiments, the plurality of wearable sensors are configured to be mounted at one of along the face, on the lip, on the head, or on the tongue.

In some embodiments, the plurality of wearable sensors are co-located.

In some embodiments, the system is configured to perform any of the above-discussed methods.

In another aspect, a non-transitory computer-readable medium is disclosed having instructions stored thereon, where the instructions, when executed by a processor, cause the processor to perform any of the above-discussed methods or systems.

BRIEF DESCRIPTION OF THE DRAWINGS

The skilled person in the art will understand that the drawings described below are for illustration purposes only.

FIGS. 4A, 4B, and 4C respectively show the positional error performance of the trained neural network of the example magnetic-based tracking and/or localization system for a training data set, a validation data set, and a testing data, respectively.

FIG. 4D shows a box plot of the errors of FIGS. 4A, 4B, and 4C.

FIG. 4E shows the positional error performance of the trained neural network of the example magnetic-based tracking and/or localization system configured with orientation compensation.

FIG. 4F shows a box plot for the non-compensated errors of FIGS. 4A-4C compared to the orientation-compensated results of FIG. 4E.

DETAILED SPECIFICATION

Each and every feature described herein, and each and every combination of two or more of such features, is included within the scope of the present invention provided that the features included in such a combination are not mutually inconsistent.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^t$ reference in the list. All references cited and discussed in this specification are incorporated herein by reference in their entireties and to the same extent as if each reference was individually incorporated by reference.

Example System

Figures 1A, 1B:
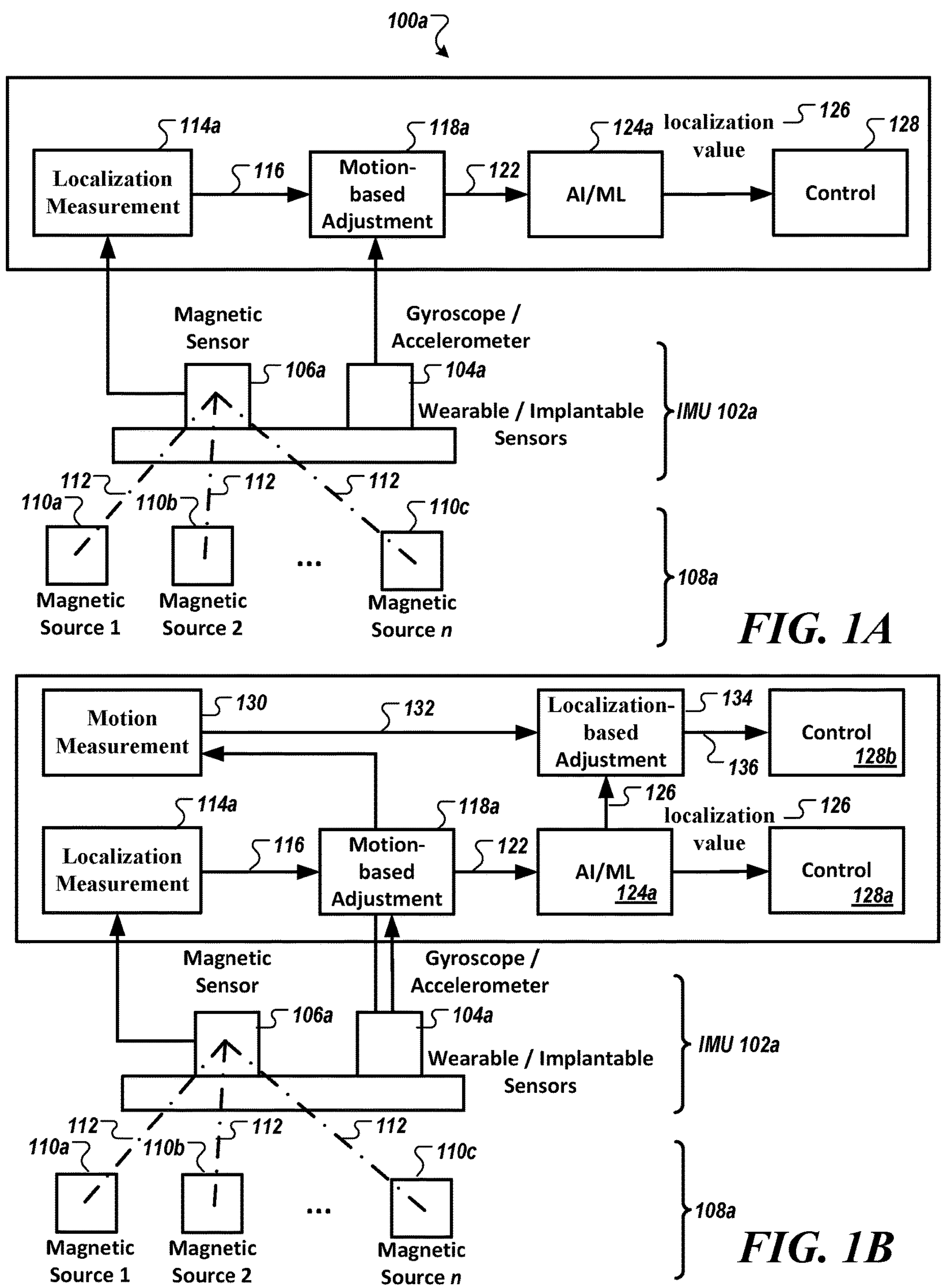
FIGS. 1A-1B each shows a diagram of a system for localization measurements for use in controls or localization applications in accordance with an illustrative embodiment.

FIG. 1A shows a diagram of a system 100 (shown as 100*a*) for localization measurements for use in controls or localization applications in accordance with an illustrative embodiment. The system includes a wearable sensor or implantation device 102 (shown as inertial measurement unit "IMU" 102*a*) that includes (i) a first wearable sensor 104 that is one of a motion sensor, an orientation sensor, or an inertial measurement sensor (shown as "Gyroscope/Accelerometer" 104*a*) and (ii) one or more magnetic sensors 106 (shown as 106*a*) that operates with a magnetic source device 108 (shown as 108*a*) that incudes one or, preferably, at least two or more local magnetic field sources 110 (shown as "Magnetic Source 1" 110*a*, "Magnetic Source 2" 110*b*, and "Magnetic Source n" 110*c*).

The local magnetic field sources 110*a*-110*c* generate a local magnetic field 112 that is sensed by the magnetic sensors 106*a* that are located nearby and that are coupled to, preferably, a magnetic sensor mixed-signal circuit 114 (shown as "Localization Measurement" 114*a*) to convert and provide raw signals 116 for localization measurement associated with the position of the magnetic sensors 106*a*. The magnetic sensors 106*a* are co-located with the other wearable sensor(s) 104*a*, which are coupled to, preferably, a motion sensor mixed-signal circuit 118 (shown as 118*a*) to (*i*) convert and provide raw signal data 120 (not shown) associated with motion-based measurements, e.g., motion measurement, orientation measurement, or an inertial measurement, and (ii) combines the raw signal data 120 with the raw signal data 116 associated with the localization measurement for calibration or adjustment of that raw signal data 116. The adjusted localization signal data 122 are provided a trained machine learned or artificial intelligence module 124 (show as "AI/ML" 124*a*) to provide output localization values 126, e.g., for controls or localization application 128 (shown as "Control" 128).

As noted above, the magnetic sensors 106*a* are co-located with the other wearable sensor(s) 104*a*. As used herein, the term "co-located" refers to the two sensor types being mounted or affixed in relation to each other on the same substrate or object. For example, the magnetic sensors 106*a* and the wearable sensor(s) 104*a* can be a part of the same semiconductor die or chip. In other embodiments, the magnetic sensors 106*a* can be located on one part of the body (e.g., tongue, face, lip), and the wearable sensor(s) 104$a$ can be located on a portion of the head that is fixed relative to the position of that magnetic sensors 106$a$.

As noted above, the local magnetic field sources 110$a$-110$c$ can generate a local magnetic field 112 that can be sensed by the magnetic sensor(s) 106$a$ that is located nearby or in proximity to the local magnetic field sources 110$a$-110$c$. In some embodiments, the local magnetic field sources 110$a$-110$c$ can be placed at the neck (e.g., in a collar device), at the back of the ear, over the head (e.g., in a cap, head band, or skin patch), in eyewear, or inside the mouth (e.g., behind the teeth or on retainers) for a sensor that is located in the mouth (e.g., on the tongue), on the lips, on the face. In other embodiments, the local magnetic field sources 110 (FIG. 5) may be placed around the wrist (or other body appendages) to provide a local magnetic field to magnetic sensor(s) 106 placed on the finger(s).

In the example shown in FIG. 1A, the system 100$a$ includes a processing unit 206 (not shown—see FIGS. 3A and 3B) coupled (wired or wirelessly) to the plurality of wearable sensors (104$a$, 106$a$) through one or more sensor interface circuitries (e.g., 114$a$, 118$a$). The processing unit includes a processor and memory having instructions stored thereon to receive a set of one or more motion-associated signals from the one or more wearable sensors; receive a set of one or more magnetic measurement associated signals from the one or more magnetic sensors; and determine a motion-associated measurement value using the one or more motion-associated signals, wherein the motion-associated measurement value has been adjusted for measurement drift based on the one or more magnetic measurement associated signals.

In some embodiments, the localization data 126 can be used to provide compensation for motion measurements. FIG. 1B shows a diagram of a system 100$b$ for localization measurements and/or motion measurement for use in controls or localization applications in accordance with an illustrative embodiment. In the example shown in FIG. 1B, similar to the system of FIG. 1A, the local magnetic field sources 110$a$-110$c$ generate a local magnetic field 112 that are sensed by the magnetic sensors 106$a$ that provide raw signals to a magnetic sensor mixed-signal circuit 114$a$ to convert and provide raw signals 116 for localization measurement. Wearable sensor(s) 104$a$ are coupled to a motion sensor mixed-signal circuit 118$a$ that converts and provides raw signal data 120 (not shown) to provide orientation compensation to the raw magnetic field localization signal data 116. The adjusted localization signal data 122 are provided to a trained machine learned or artificial intelligence module 124$a$ to provide output localization values 126, compensation of the motion measurement.

In the example of FIG. 1B, the raw signals from the wearable sensor 104$a$ are additionally received by a motion sensor mixed-signal circuit 130 (shown as "Motion Measurement" 130$a$) to convert and provide raw signal data 132 for motion measurement. The output localization values 126 are combined with the motion raw signal data 132 in a localization-based adjustment operation 134 to provide an adjusted motion value 136, e.g., for controls or localization application 128 (shown as "Control" 128$b$). Motion measurements, e.g., gyroscope and accelerometer, can provide high fidelity measurements but can be affected by drifts. That is, over the course of long sensor acquisitions, "positional drift" can accumulate small sensor errors over time when the position is calculated from the raw signals. By leveraging the localization value 126, the system 100$b$ can compensate for these sensor error drifts over time.

Example Method of Tracking

Figure 2A:
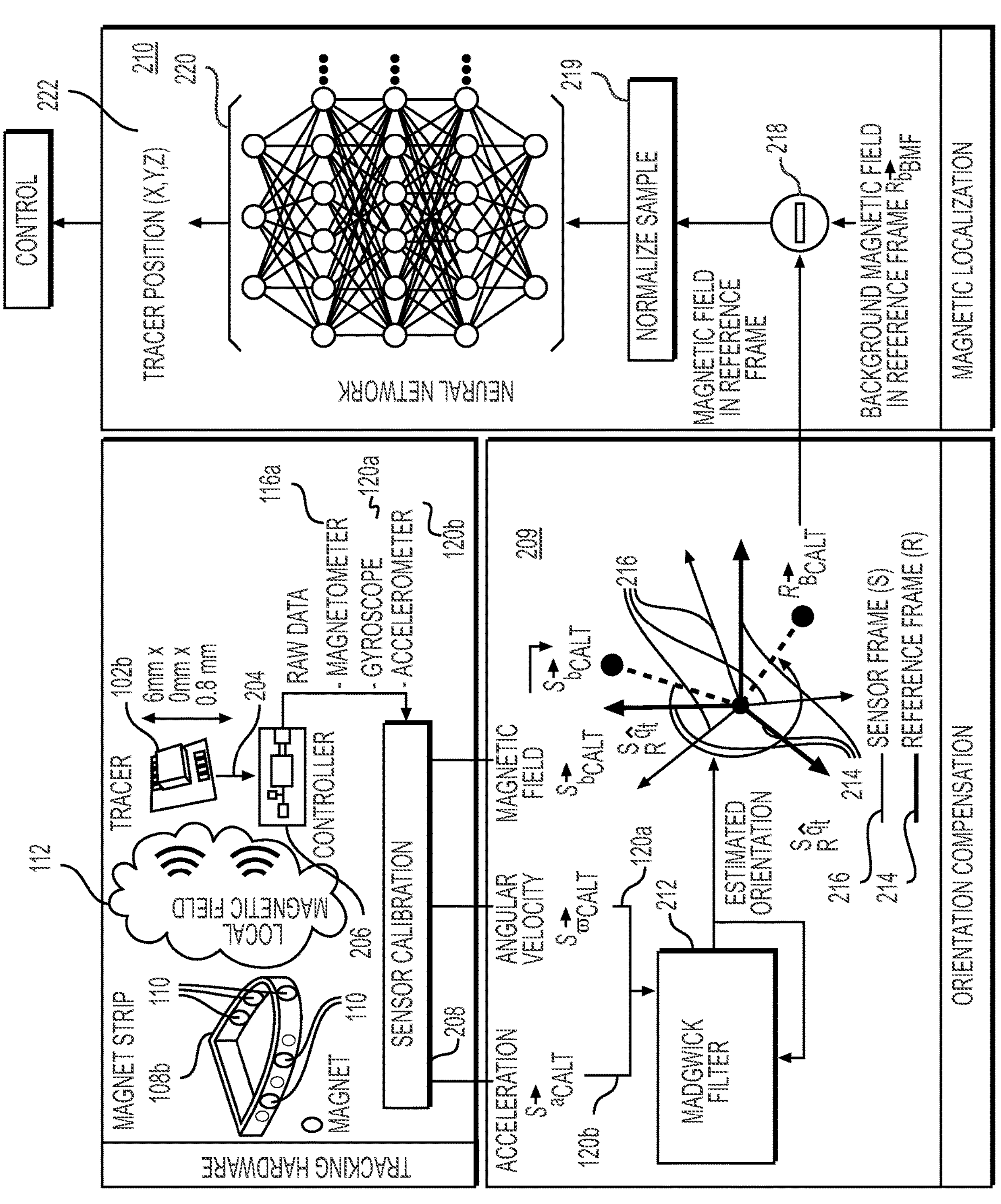
FIG. 2A shows an example magnetic-based tracking and/or localization operation of the systems of FIG. 1A or 1B using magnetic-based measurements with orientation compensation from angular velocity and acceleration measurement in accordance with an illustrative embodiment.
Figure 2B:
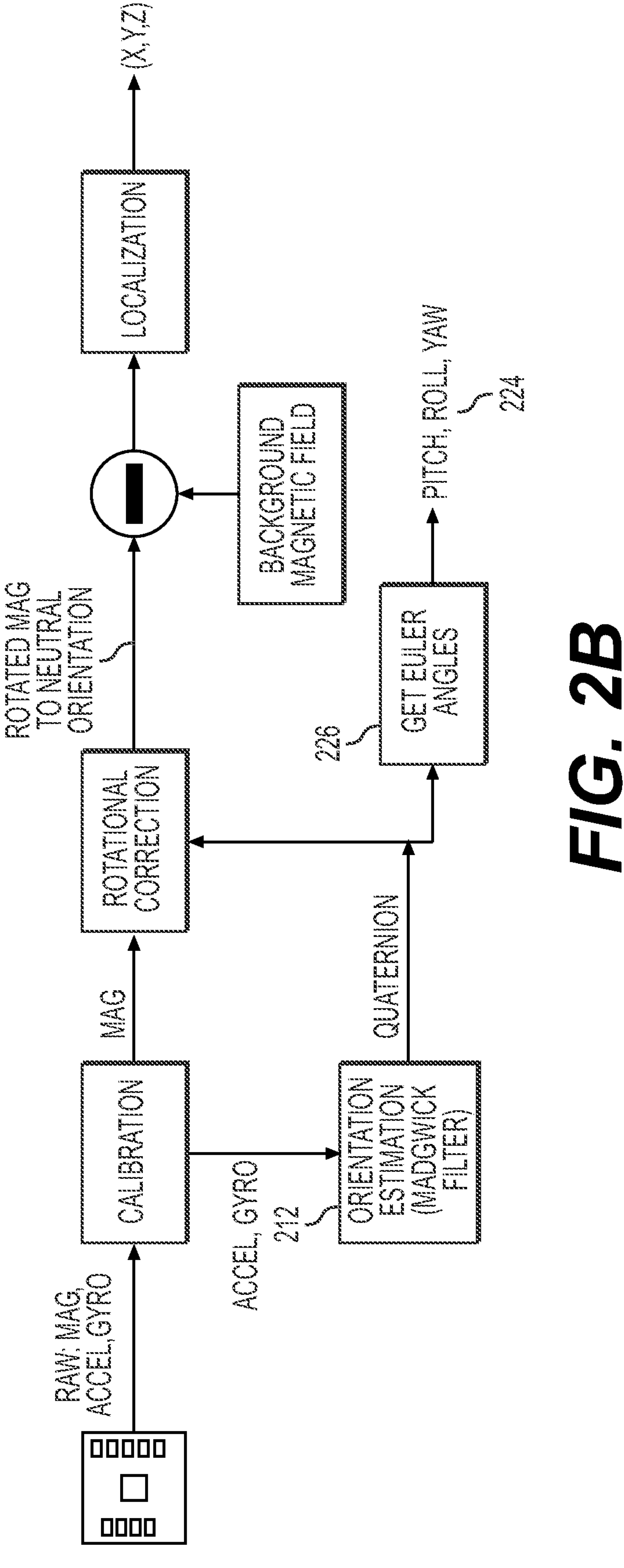
FIG. 2B shows another example of the tracking and/or localization operation of FIG. 2A in accordance with an illustrative embodiment.

FIG. 2A shows an example magnetic-based tracking and/or localization operation 200 of the systems of FIG. 1A or 1B using magnetic-based measurements with orientation compensation from angular velocity and acceleration measurement. FIG. 2B shows another tracking and/or localization operation 200.

In the example shown in FIG. 2A, the magnetic sensor 106 (not shown) is integrated with wearable sensors 104 comprising an angular velocity measurement sensor 202 (also referred to as a "gyroscope" sensor, not shown) and acceleration measurement sensor 204 (also referred to as an "accelerometer," not shown) on a single IMU (shown as "tracer" 102$b$). The magnetic sensor 106 operates with a set of one or more magnets sources 110 located on a magnetic source device 108 (shown as "magnet strip" 108$b$) that generates a local magnetic field 112 within a localization sensing area that the tracer 102$b$ is placed.

The tracer 102$b$ is operatively coupled, via a cable or wirelessly communication, to a controller 206 that convert the signals (204) from the sensors (e.g., 106, 202, 204—not shown) to raw sensor data (shown as raw "magnetometer" or "magnetic field" data 116$a$, raw "gyroscope" or "angular velocity" data 120$a$, and raw "accelerometer" or "acceleration" data 120$b$). The controller 206 executes a sensor calibration operation 208 (that compensates the magnetic measurements based on orientation measurement), an orientation compensation operation 209, and a magnetic localization operation 210.

Sensor Calibration.

In the example shown in FIG. 2A, the sensor calibration operation 208 includes a Madgwick orientation filter 212 that receives raw acceleration data $s_{\vec{a}_{cal,t}}$ 120$b$ and raw angular velocity data $s_{\vec{\omega}_{cal,t}}$ 120$a$ to generate an estimated orientation $$ {}^{S}_{R}\hat{q}_t $$

that provides a reference frame (216) for the magnetic sensor frame (214). The Madgwick filter generates a quaternion representation of orientation to describe the nature of orientations in three dimensions. The calibration can address the non-idealities inherent to the sensors to provide millimetric accuracy for such sensors. To calibrate the accelerometer ($\vec{a}_{raw}$), an ellipsoid fit method can be used, e.g., to provide a 3×3 gain matrix ($G_a$) and a 3×1 offset vector ($\vec{O}_a$) [20]. To calibrate the gyroscope ($\vec{\omega}_{raw}$), a computer vision method can be used based on colored markers to estimate the angular position of the IMU relative to a reference point. In another method, a motorized gimbal can be used to rotate the gyroscope along each axis of rotation, and an encoder is used to estimate the reference angles. In other method, the angles may be used as reference values to derive an optimal gain matrix ($G_\omega$) and an offset bias ($\vec{O}_\omega$) using a least square error method on the estimated angles by the gyroscope. The IMU can be rotated in all directions while the magnetometer data is collected. To calibrate the magnetometer ($\vec{b}_{raw}$), the ellipsoid described by the 3-axis magnetic readings may be then generated using an ellipsoid fit method [21] to return a 3×3 gain matrix ($G_m$) and a 3×1 offset bias ($\vec{O}_m$). The resulting sensor calibration parameters $\vec{a}_{cal}$, $\vec{\omega}_{cal}$, $\vec{b}_{cal}$ can be determined as a set of linear transformations, e.g., per Equation 1, and later applied in the sensor calibration operation 208.

$$\vec{a}_{cal} = G_a x \vec{a}_{raw} - \vec{O}_a \quad \text{(Eq. 1)}$$

$$\vec{\omega}_{cal} = G_\omega x \vec{\omega}_{raw} - \vec{O}_\omega$$

$$\vec{b}_{cal} = G_m x \vec{b}_{raw} - \vec{O}_m$$

Orientation Compensation. The magnetic-based tracking and/or localization operation 200 is configured to perform background magnetic field (BMF) 218 cancellation prior to feeding the orientation-compensated magnetic values into the localization model (e.g., machine learning or neural network). The BMF can include both the Earth's magnetic field, which can vary with the location on the Earth and time [22], as well as vary due to nearby magnetic sources (e.g., ferromagnetic materials). In prior permanent magnet localization (PML) applications, the magnetometers are fixed in place, which simplifies the BMF cancellation process by capturing the BMF with no magnet in the vicinity of the sensors [18], [19]. However, in a movable configuration of the magnetometers, the BMF can be seen as a rotating vector in a magnetometer's viewpoint.

To cancel the BMF with a movable magnetic sensor, the orientation compensation operation 219 may use the magnetometer's orientation analytically derived from the accelerometer and magnetometer data (magnetic field raw data ${}^{S}\vec{b}_{cal,t}$ 116*a*) to determine the magnetic field in a reference frame 215 that can then be used to cancel BMF 218 prior to being fed to the localization model (e.g., optimized gradient-descent algorithm, neural network, or other machine learning). In doing so, the resulting model is simplified and complexity reduced (since different combinations of position and orientation produce the same magnetic field) as compared to the magnet being rotated in various orientations when training a localization algorithm in [19]

The magnetic field read by a magnetic sensor can be dependent on both the position and orientation of the magnetic source. In an IMU configuration, the IMU measurement ${}^{S}a$, ${}^{S}b$, and ${}^{S}\omega$ provide 3 angular positions thus the number of unknown variables can be reduced, e.g., from 6 (3 positions and 3 angles) to 3 positions only (X, Y, Z). In other PML method, all 6 variables are unknown and were estimated together using the magnetic readings. Here, the Madgwick filter can be used to estimate the tracer's orientation in a straightforward and computationally efficient implementation. The orientation can be expressed as the rotation from the sensor frame (S) (216) to a reference frame (R) (214) set to be orthogonal to Earth's gravity vector to provide an absolute value of 0° for pitch and roll. Because the magnetometer may already be used for magnetic localization and, in the presence of a strong local magnetic field, the tracer's yaw cannot be determined with absolute value by estimating the tracer's heading using the Earth's magnetic poles. In the exemplary reference frame, the zero yaw can be set to be aligned with the major axis of a magnet strip. The orientation can be represented as a quaternion $$({}^{S}_{R}\hat{q}_t),$$

estimated from the calibrated acceleration and angular velocity, and a tuning parameter sets the robustness of the filter against sensor noise. For an example IMU, a value of 0.071 for the tuning parameter was observed to result in the estimation accuracy of 1.09°, 1.04°, and 1.10° root-mean-square errors for the pitch θ, roll ϕ, and yaw ψ, respectively.

Magnetic Localization. The orientation-compensated magnetic localization may be used to estimate orientation to rotate the measured magnetic field from the sensor frame (${}^{S}\vec{b}_{cal}$) to the reference frame (${}^{R}\vec{b}_{cal}$) using the standard equation for quaternion rotation per Equation 2:

$${}^{R}\vec{b}_{cal,t} = {}^{S}_{R}\hat{q}_t \otimes {}^{S}\vec{b}_{cal,t} \otimes {}^{S}_{R}\hat{q}_t^* \quad \text{(Eq. 2)}$$

where ⊗ and * denotes quaternion multiplication and conjugate, respectively.

The same rotation information can be applied to the BMF cancellation operation, which can be collected prior to the start of a data collection and with no magnet strip in the tracer's vicinity. Once both are in the same reference frame, the BMF can be subtracted from the magnetic field, and the resulting orientation and BMF compensated magnetic field can be fed into a feedforward neural network responsible for estimating the tracer's 3D position X, Y, and Z (222). Prior to being fed into the neural network, the magnetic values can be normalized (219), e.g., to be in the range of ±1.0.

The magnetic-based tracking and/or localization operation 200 can train the neural network (220) by collecting magnetic samples of the tracer traversing a trajectory with predefined positions as the reference. The L2 norm of the difference between the 3D position estimated by the model ($\vec{p}_{est}$) and its reference ($\vec{p}_{ref}$) can be used as the loss function ($E_{pos}$) to be minimized during training, per Equation 3.

$$E_{pos} = \|\vec{p}_{est} - \vec{p}_{ref}\| \quad \text{(Eq. 3)}$$

Training may be halted when the validation Q3 error did not improve after 100 epochs to prevent overfitting to the training set. In one embodiment, it was empirically observed that the architecture of the neural network that provides the lowest errors included 2 hidden layers, 40 neurons per layer, soft-plus activation function, and RMSprop as the optimizer with 256 batch size and 0.05 learning rate.

Pitch, Roll, Yaw Output.

FIG. 2B shows that pitch, roll, and yaw orientation data (224) can also be generated from the operation of FIG. 2A by calculating the Euler angles (226) from the output of the Madgwick filter.

Example Tracking System and Hardware

Figure 3A:
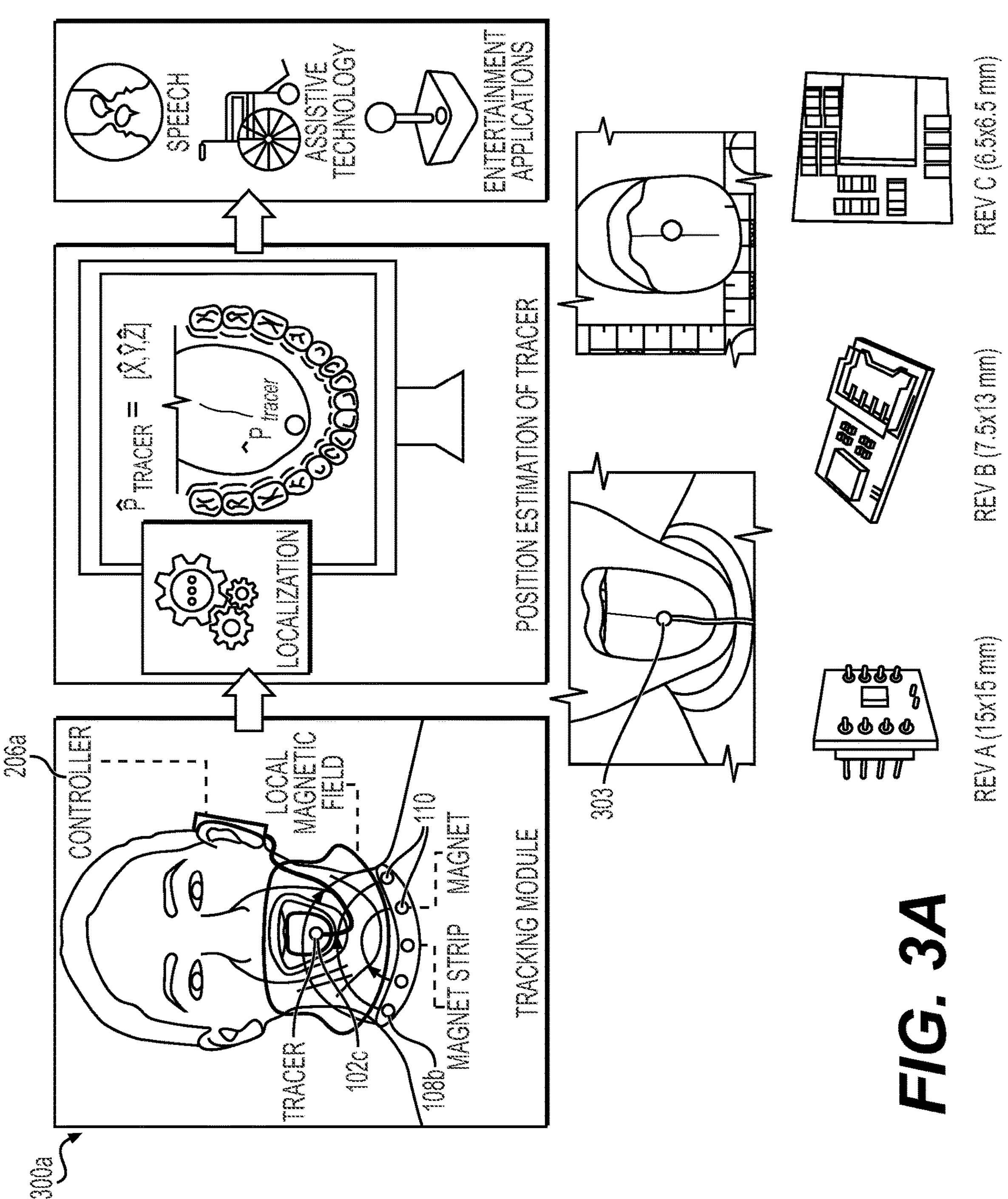
FIG. 3A shows an example magnetic-based tracking and/or localization system for the control of assistive technology in accordance with an illustrative embodiment. It can be used in other applications such as speech rehabilitation and entertainment applications or other applications described herein.

FIG. 3A shows an example magnetic-based tracking and/or localization system 300 (shown as 300*a*), e.g., configured for speech rehabilitation, control of assistive technology, or entertainment applications or other applications described herein.

System 300*a* includes a wearable/implantable sensor 102 (shown as 102*c* that is positioned on a user's tongue. System 300*a* includes a magnetic source device 108 (shown as "magnet strip" 108*c* that has a plurality of magnetic sources 110. The magnet strip produces a local magnetic field to provide localization of the tracer in the subject's mouth. The tracer includes an inertial measurement unit that connects to a controller 206 (shown as 206*a*) configured to be placed behind the user's ear in this example. The controller 206*a* is configured to execute the localization algorithm to estimate the 3D position and/or 3D orientation of the tracer, e.g., as described in relation to FIG. 2A. Additional tracers (e.g., located at the lips or on the face or chin) may be added to be tracked simultaneously by the controller 206*a*. The system 300 is portable to be used in activities of daily living.

System 300*a* employs an integrated inertial measurement unit (IMU), e.g., comprising a magnetometer, an accelerometer, and a gyroscope, as a tongue tracer that can move in a local magnetic field generated by a magnet strip composed of an array of permanent magnets. The IMU can be used by the controller 206*a* to perform a reverse PML operation in which the local magnetic field is held constant while the magnetometer is moving within this field. The reversed PML allows for the local magnetic field to be shaped without changing the features of the tracer (e.g., dimension, shape). In a preferred embodiment, multiple permanent magnets or electromagnets may be used, each as a magnetic field source. In other embodiments, a single permanent magnet or electromagnet can be shaped to provide the local magnetic field.

The system (e.g., 300*a*) can be configured with an expanded operational range. By increasing the magnetic field intensity of the magnetic field sources (e.g., 110), e.g., by increasing the number or size of magnetic field sources (e.g., 110), the magnetic field device 108 (e.g., strip 108*b*) can be placed further away from the user's head or neck, e.g., at the back of the ear, over the head (e.g., in a cap, head band, or skin patch), in eyewear, or inside the mouth (e.g., behind the teeth or on retainers).

In the example shown in FIG. 3A, the strip 108*b* can be hidden in a neckband or behind or around the ear. Tracers can be tracked independently because each tracer provides its own position and orientation information. Additionally, the accelerometer and gyroscope readings can be used to estimate the orientation of the tracer to re-orient the sensor's magnetic field reading to a reference frame. The orientation-compensated magnetic field can then be used to estimate the position of the tracer by a feedforward neural network or machine learning model or other models as described herein. The tracer can be wired or can be configured with a transmitter to operate wirelessly with the controller 206*a*. The system can be used to provide tracking accuracy in a volume greater than a typical oral cavity (8 cm×8 cm×5 cm) with a tracer being rotated by ±50° for both pitch and roll, which are the rotations of interest for the tongue.

A hardware prototype has been developed that includes a magnet strip, a tracer, and a controller. The magnet strip is a custom-designed and 3D-printed semi-ellipse with a length of 6 cm and a width of 7 cm. In the prototype, five permanent magnets are evenly distributed around the strip, as shown in FIG. 3A. Each magnet (model D32-N52, manufactured by K&J Magnetics, Pipersville, Pennsylvania) is cylindrical, N52 grade, and measures 4.8 mm in diameter and 3.2 mm in thickness. Because of the geometric arrangement of the magnets, the magnet strip generates a unique and local magnetic field. These dimensions, numbers, position, and orientation of the magnets are chosen empirically, and other configurations can be employed.

In the prototype, the tracer includes an LSM9DS1 inertial measurement unit (manufactured by STMicroelectronics, Geneva, Switzerland) that can measure 3-axis acceleration, 3-axis angular velocity, and 3-axis magnetic field. The IMU is embedded in a custom printed circuit board (PCB) with a size of 6 mm×6 mm×0.8 mm. The tracer is wired to a controller 206*a* manufactured by Teensy microcontroller (PJRC, Sherwood, OR) and a custom PCB to provide a wire connection to the tracer. Custom firmware was developed for obtaining the IMU's data using the I2C communication protocol and transmitting raw data packets to a host computer every 10 ms for further processing. In FIG. 3A, a different version of the IMU is shown. Each is configured as a portable device.

Figure 3B:
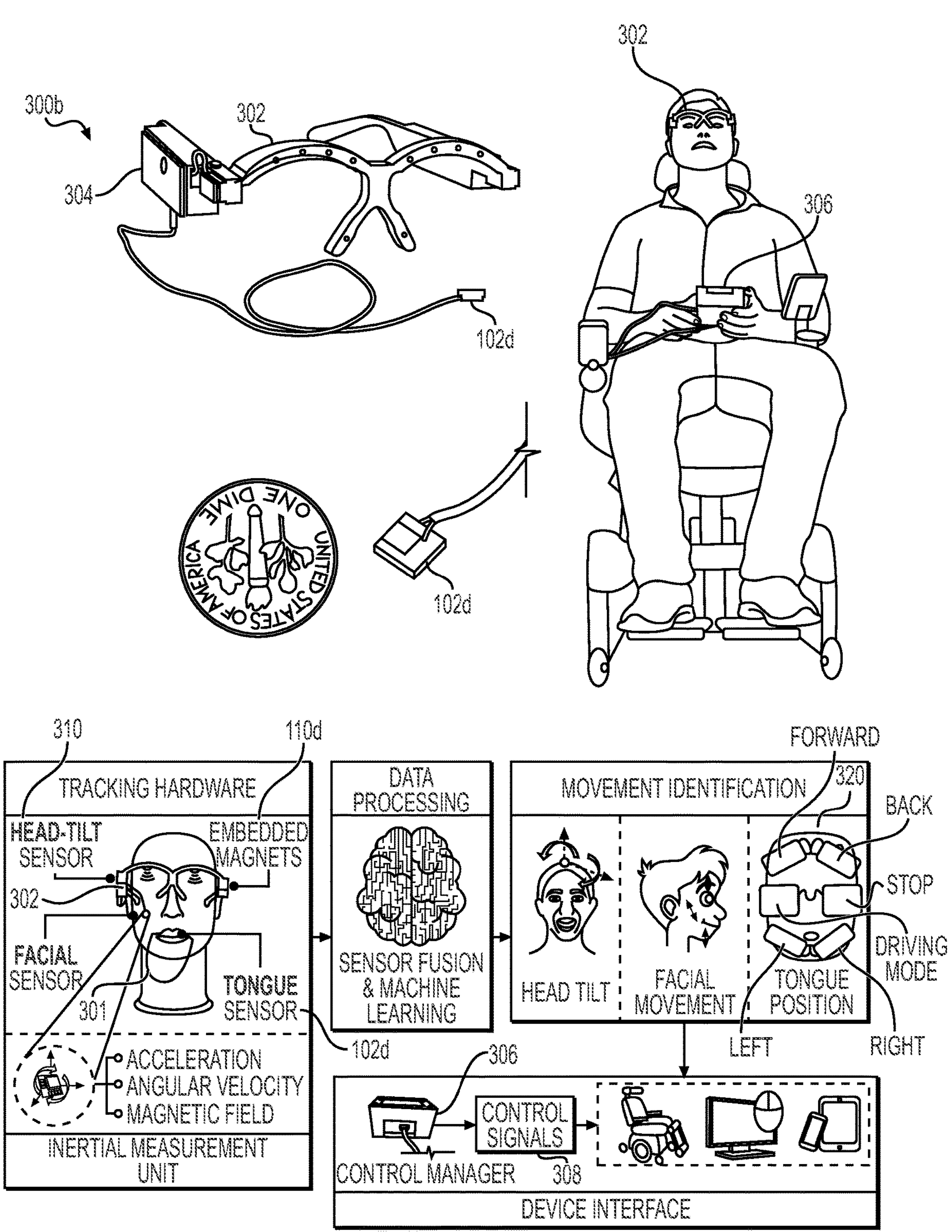
FIG. 3B shows an example magnetic-based tracking and/or localization system for a wheelchair drive controller in accordance with an illustrative embodiment.
Figure 3B:
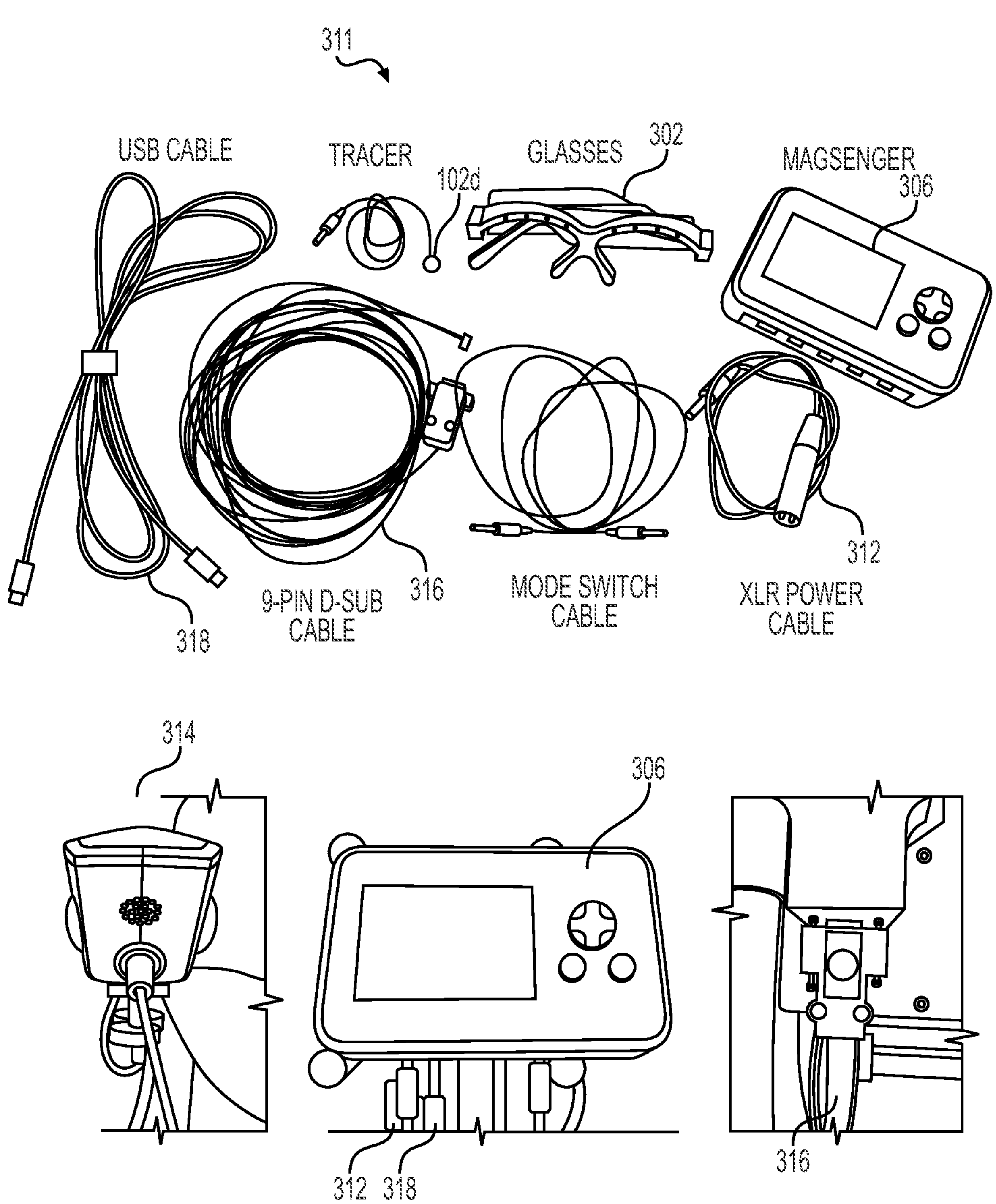

FIG. 3B shows an example magnetic-based tracking and/or localization system 300 (shown as 300*b*) for a wheelchair drive controller in accordance with an illustrative embodiment. It can also be used for speech rehabilitation, entertainment applications, or other applications described herein. In the example of FIG. 3B, the wearable/implantable device 102 (shown as 102*d*) is configured as a tracer IMU to be placed on the tongue, e.g., with PeriAcryl tissue adhesive (see diagram 303—FIG. 3A). The tracer IMU is connected via cable 301 to a controller 206 (shown as 206*b*) configured on an eyewear frame 302. The tracer IMU may alternatively include a transmitter to wirelessly operate with the controller 206*b*. The eyewear frame 302 includes a compartment 304 to house the controller 206*b*. The controller 206*b* operates over a wire communication with a power wheelchair controller manager 306 that provides control signals 308 to a local controller of a powered wheelchair. The eyewear frame 302 includes the set of permanent magnets (shown as 110*d*) as the magnetic field sources. The eyewear frame 302 also includes a set of sensor(s) 310 to provide head orientation/tilt measurement. The sensors 310 can provide orientation or tilt measurements that can be used to remove any external orientation effects from the movement of the user on surfaces that are at an angle. With the permanent magnets 110*d* fixable mounted on the eye frame 302, and the eye frame 302 being fixable placed on the user, the tongue tracer 102*d* has a fixed frame of reference with respect to the head. However, as the head is subject to a tilt when the wheelchair and user are driving on an angled or inclined surface, the additional orientation sensor 310 provides measurements to remove that reference frame from the other orientation measurements by the IMU.

Wheelchair Drive Controller:

MagTrack. The magnetic-based tracking and/or localization system 300*b* can be used in a wheelchair drive controller (also referred to as the "MagTrack" system) that can provide a complex human-machine interface to external systems such as a power wheelchair to autonomously perform important activities of daily living. Rather than the controller being bound to a wheelchair, which may force the users to remain on the wheelchair to access their devices, the magnetic-based tracking and/or localization system 300*b* is configured as an external wearable system that can interface to the controls of the power wheelchair and track multiple motion inputs (head, tongue, cheek, jaw, etc.). The user can thus control and switch between devices in their surroundings. Since MagTrack is wearable, the users can control devices from anywhere. The system can be designed for quadriplegics and paraplegics. In other embodiments, the wheelchair drive controller is integrated into a wheelchair device.

The controller 206*b* is configured to provide sensor readings at 10 ms resolution. The localization algorithm and hardware can operate at a sampling of at least 100 Hz, e.g., 200 Hz, e.g., for the accelerometer and gyroscope measurement, and at about 80 Hz for the magnetometer measurement. The localization algorithm is efficient to operate and can operate at higher sampling with faster sensors.

The components of the magnetic-based tracking and/or localization system **300*b* as a wheelchair drive controller are shown in diagram 311. System 300*b* includes the tracer 102*d*, the eyewear frame 302, and the power wheelchair controller manager 306 discussed above. The system 300*b* further includes a power cable 312, e.g., XLR cable, that can connect the power wheelchair controller manager 306 to a charging port of the wheelchair (see diagram 314). The system 300*b* further includes a display/support cable 316 that can connect the power wheelchair controller manager 306 (e.g., via an 8-pin header) to a secondary display (e.g., via a 9-pin port). The system 300*b* further includes a cable 318 (e.g., USB cable) that can connect the eye wear frame 302 to the power wheelchair controller manager 306**.

The controller manager 306 is configured to receive sensor readings (e.g., tracer position X, Y, Z; eyewear orientation roll, yaw, pitch) from controller **206*b*** and to translate the sensor readings to specific command signals for the wheelchair driver controller.

Table 1 shows a set of control modes for the wheelchair drive controller that are user selectable.

TABLE 1

| | Tongue Only | Head Only | Combo 1 | Combo2 |
|---|---|---|---|---|
| Tongue Driving | X | | X | |
| Tongue Steering | X | | | X |
| Head Driving | | X | | X |
| Head Steering | | X | X | |
| Tongue Latch | X | X | X | X |
| Tongue Stop | X | X | X | X |
| Tongue Profile | X | X | X | X |

In the "tongue only" mode, the tongue measurement (via tracer **102*d*) is used entirely to control the wheelchair. To drive, the user can place the tongue on the upper left and right commands (see diagram 320—FIG. 3B) to move the wheelchair in the forward and backward directions, respectively. The longer the tongue is placed in the forward and backward positions, the faster the wheelchair will drive in the respective direction. The controller manager can provide latch and unlatch commands. The unlatched command can direct the wheelchair to stop driving when the tongue returns to the neutral/idle position. The latched command can direct the wheelchair to continue driving once the tongue returns to neutral. To steer, the user can place the tongue in the lower left and right commands (see diagram 320**) to steer the wheelchair in the left and right directions, respectively. The longer the tongue is placed in either of these positions, the faster the wheelchair is directed to turn in that direction. The steering is always in unlatched mode.

In "head only" mode, the head sensor is used to drive and to steer the wheelchair using orientation sensors 310 located on the eyewear frame. The tongue measurement via the tracer **102*d*** can still be used to latch and stop the wheelchair, as well as navigate through the profiles. In this mode, driving and steering are only activated once the user tilts their head about halfway between their resting position and calibrated head position. To drive, the user can tilt the head forward or backward past halfway between the user's resting position and the calibrated forward and backward head positions, respectively. In the unlatched mode, when the head is sufficiently tilted, the head proportionally controls the forward or backward speed of the wheelchair. Returning the head to the resting position stops the wheelchair. In the latched mode, the user can tilt their head forward or backward for a brief moment increments the wheelchair's speed in that respective position. The wheelchair continues to move in the commanded direction even when the head returns to the resting position. To steer, the user can tilt the head left or right steers the wheelchair in the respective direction proportionally. Returning the head to the rest position stops steering the wheelchair.

In the "Combination 1" mode, the user can drive using the tongue and steer using the head. To drive, the user can place the tongue on the upper left and right canine to move the wheelchair in the forward and backward directions, respectively. The longer the tongue is placed in the forward and backward positions, the faster the wheelchair will drive in the respective direction. To steer, the user can tilt the head left or right to steer the wheelchair in the respective direction proportionally. Returning the head to the rest position stops steering the wheelchair.

In the "Combination 2" mode, the user can drive using the head and steer using the tongue. To drive, the user can tilt the head forward or backward past halfway between the user's resting position and the calibrated forward and backward head positions, respectively. To steer, the user can place the tongue in the lower left and right canine to steer the wheelchair in the left and right directions, respectively. The longer the tongue is placed in either of these positions, the faster the wheelchair will turn in that direction.

MagTrack Software Calibration—Head Calibration.

The controller manager 306 can allow for control of the wheelchair using head movements for selected modalities. To allow for comfortable head movements, the system can calibrate to the user's range of movement of the head. During the calibration, the controller manager 306 can acquire the head position at the rest position, the chin down position, the chin-up position, the left position, and the right position, to determine the full range of measurement of the orientation 310.

MagTrack Software Calibration—Tongue Calibration.

To use the controller manager 306 with the tongue, the controller manager 306 can calibrate the tongue position. The system can instruct the user to speak or mouth a short passage, then place the tongue in a variety of positions in the mouth. The passage recitation by the user provides a sensing framework to detect when the user is speaking that ensures that the system does not activate the wheelchair while the user is speaking. The calibration also determines the position of the tongue for a number of designated positions are reserved for controlling the wheelchair. The designated positions can include the Upper Left Molar (UL), the Upper Right Molar (UR), the Lower Left Molar (DL), the Lower Right Molar (DR), the Left Cheek (LS), and the Right Cheek (RS). For all teeth positions, the tracer can be touched to an inside part of the tooth, not just the tongue. For the cheek positions, the user can gently push against their cheek such that a protrusion is noticeable.

Figure 3C:
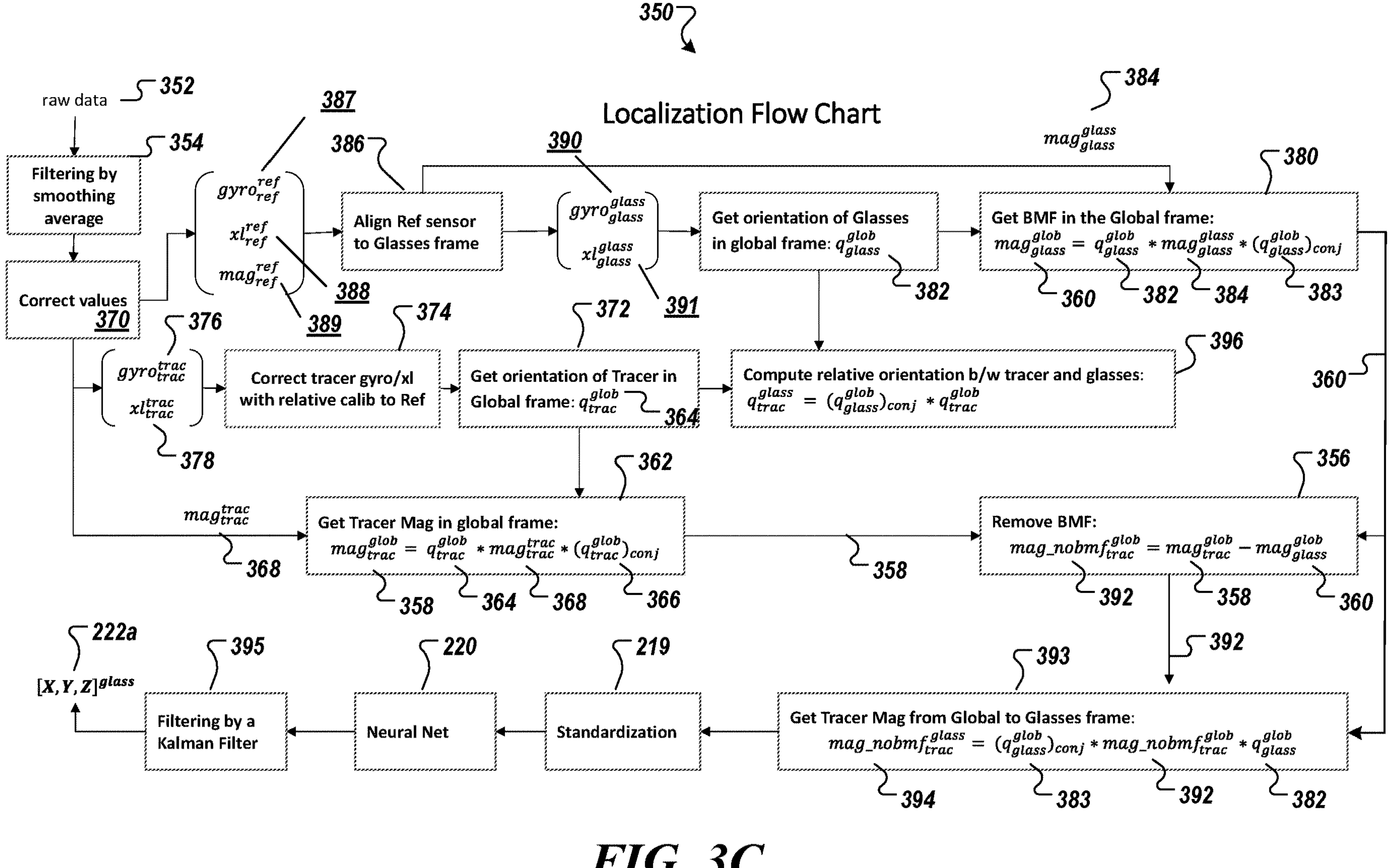
FIG. 3C shows an example tracking and localization operation for the system of FIG. 3B in accordance with an illustrative embodiment.

MagTrack Tracking and Localization Operation. FIG. 3C shows an example tracking and localization operation 350, e.g., for the system of FIG. 3B. In the example shown in FIG. 3C, the raw data 352 (e.g., having the raw acceleration ("xl") data $^{S}\vec{a}_{raw,t}$ **120*b*, raw angular velocity ("gyro") data $^{S}\vec{\omega}_{raw,t}$ 120*a*, and raw magnetic field ("mag") data $^{S}\vec{b}_{raw,t}$ 116*a*—see FIG. 2A) are received and smoothed by a smoothing average (354**).

To remove the background magnetic field (356) to provide a normalized magnetic field data 392, operation 350 determines the magnetic field data of the tracer at the global frame $(mag_{trac}^{global})$ (358) and the magnetic field data of the glasses at the global frame $(mag_{glass}^{global})$ (360) and subtract them.

To determine (362) the tracer magnetic field in the global frame $(mag_{trac}^{global})$

358, the orientation of the tracer in the global frame $(q_{trac}^{global})$ (364) and its conjugate $(q_{trac}^{global})_{conj}$ (366) can be multiplied to the magnetic field data of the tracer at the tracer frame $(mag_{trac}^{trac})$ (368), determined from a correction operation 370, e.g., as described in relation to FIG. 2A. To determine (372) the orientation of the tracer in the global frame $(q_{trac}^{global})$ (364), operation 372 may determine as a quaternion using an orientation estimator (e.g., Madgwick filter) on outputs from a correction (374) of the tracer gyroscope and accelerometer measurement $(gyro_{trac}^{trac})$ (376) and $(xl_{trac}^{trac})$ (378), provided from the correction operation 370, with relative calibration to the reference frame.

To determine (380) the magnetic field data of the glasses at the global frame $(mag_{glass}^{global})$ (360), the background magnetic field in the global frame may be determined by multiplying the orientation of the glass in the global frame $(q_{glass}^{global})$ (382) and its conjugate $(q_{glass}^{global})_{conj}$ (383) to the magnetic field data of the glass at the glass frame $(mag_{trac}^{glass})$ (384). The magnetic field data of the glass at the glass frame $(mag_{trac}^{glass})$ (384) may be determined by aligning (386) the reference sensors input $((gyro_{ref}^{ref})$ (387), $(xl_{ref}^{ref})$ (388), $(mag_{ref}^{ref})$ (389)) to the glass frame. The reference sensors input $((gyro_{ref}^{ref})$ (387), $(xl_{ref}^{ref})$ (388), $(mag_{ref}^{ref})$ (389) may be acquired from sensor 310 described in relation to FIG. 3B. The orientation of the glass in the global frame $$\left(q_{glass}^{global}\right)$$

(382) can be determined as a quaternion using an orientation estimator (e.g., Madgwick filter) using the gyroscope reading of the glass in the glass reference frame $$gyro_{glass}^{glass}$$

(390) and the accelerometer reading of the glass in the glass reference frame $$xl_{ref}^{ref}$$

(391).

To determine (393) the magnetic field of the tracer at the glass reference frame mag_nobm $$f_{trac}^{glass}$$

(394), the orientation of the glass in the global frame $$\left(mag_{glass}^{glob}\right)$$

(382) and its conjugate $$\left(q_{glass}^{glob}\right)_{conj}$$

(383) can be multiplied to the normalized magnetic field data of the tracer at the global frame $$\left(\text{mag\_nobm}_{trac}^{glob}\right)$$

(392). The normalized magnetic field data 394 can be adjusted 219 to a normalized data range and then provided to a trained neural network model 220 (shown as "Neural Net" 220), to provide the position outputs X, Y, Z (222*a*) of the tracer with respect to the glass reference frame. The output of the neural network model 220 can be filtered (395), e.g., by a Kalman filter. In the example of FIG. 3C, the relative orientation of the tracer between the tracer and the glasses can also be determined (396).

Figure 5:
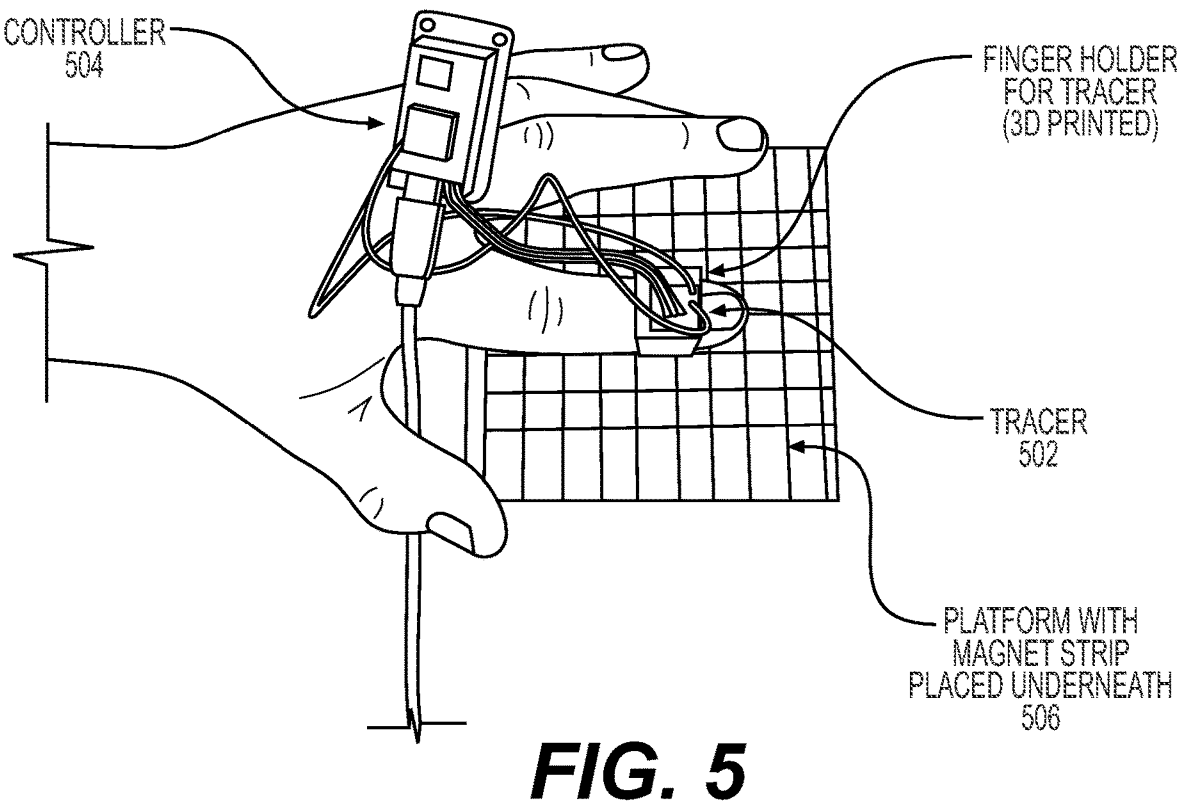
FIG. 5 shows an example magnetic-based tracking and/or localization system for a computer human-machine interface (HMI) controller in accordance with an illustrative embodiment.

Hand-Based Controller. The magnetic-based tracking and localization method and system as described herein may be employed, for example, as a hand control. FIG. 5 shows an example implementation that includes a controller 206*a* (shown as 502) and tracers 102 (shown as 504). The controller 502 may be integrated into a glove or a wrist ban. The tracers 102 can be placed at the fingertips to provide localization measurement of the fingers. The magnetic field sources 110 can be placed at the controller 502 or in an external object such as a hand rest.

Experimental Results and Examples

A study was conducted to evaluate the performance of the exemplary magnetic-based tracking and/or localization operation and system. The study employed the metric used in [19] in which accuracy is represented as a positional error defined by the L2 norm of the difference between the actual and estimated 3D position of the tracer, as expressed in Eq. 3.

Figure 6:
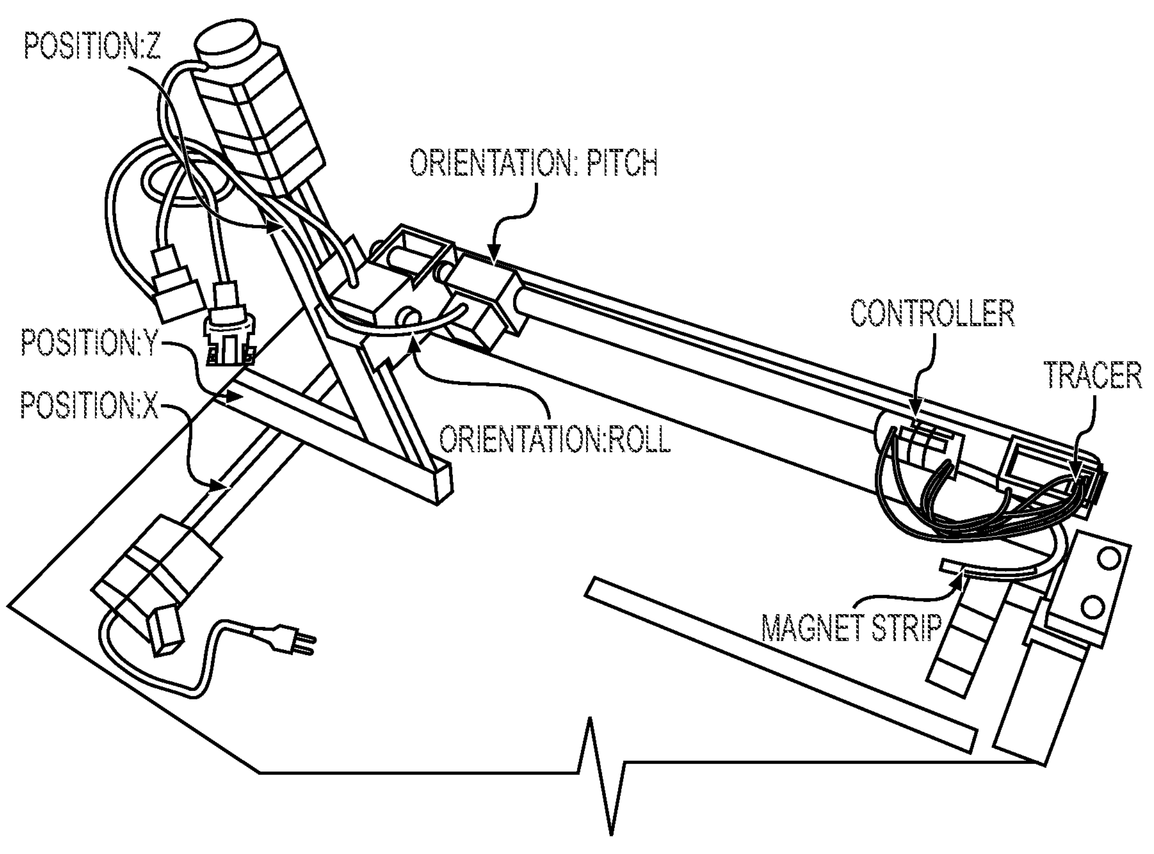
FIG. 6 shows a test rig comprising a multi-degree-of-freedom positioning stage that was used in a study to collect the datasets to train a neural network model for magnetic tracking and localization in accordance with an illustrative embodiment.
Figure 6:
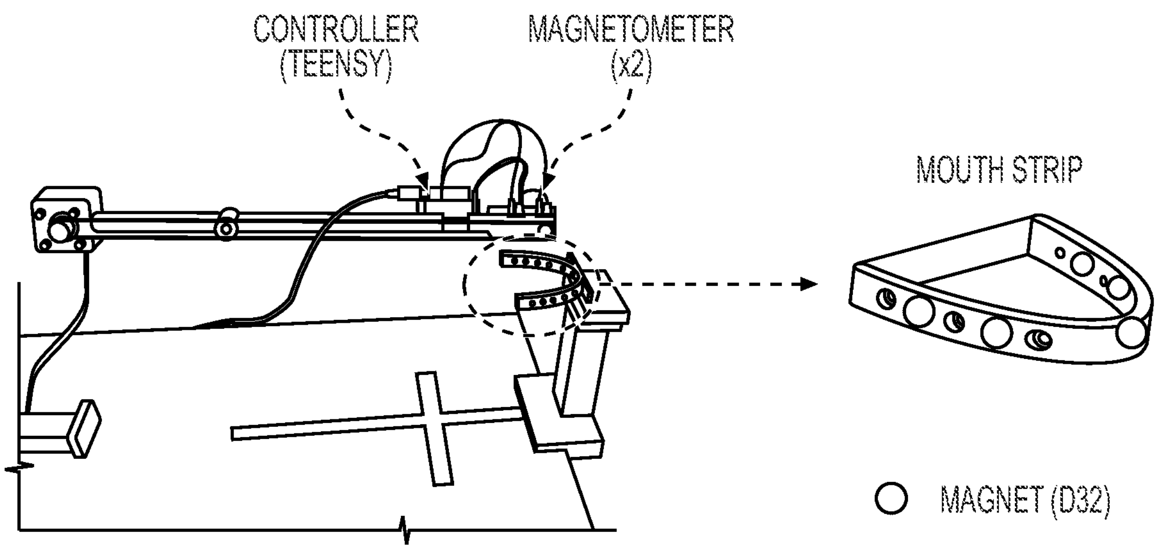

Machine Learning Training Data Test Environment. To collect the datasets needed to train the neural network and evaluate the tracking accuracy of the exemplary method and system, a 5D positioning stage was developed to acquire data set from the tracer at corresponding positions and orientation. FIG. 6 shows a test rig comprising a 5 degree-of-freedom positioning stage that was used to collect the datasets to train a neural network model for magnetic tracking and localization.

5D Positioning Stage. The 5 degree-of-freedom positioning stage was redesigned for this study from that described in [19]. The linear stage includes three motorized XSlides (Velmex Inc., Bloomfield, NY, USA) that can position the tracer in the 3D space (X, Y, and Z) with a reported accuracy of 76 μm. The rotational stage is capable of orienting the tracer along its pitch and roll thanks to a pulley/belt system driven by two stepper motors in half-step mode, resulting in an accuracy of 0.9°. In the current configuration, the yaw cannot be changed because of many practical issues. The motor can be placed far enough from the tracer (>15 cm) to prevent their induced magnetic field from being read by the magnetometer. This prevents any practical design based on standard motors but could be overcome in the future with the use of nonmagnetic piezoelectric motors.

Training for Magnetic Localization. Training and evaluating the accuracy of the neural network in estimating the position of the tracer require three separate datasets: a training (FIG. 4*a*), validation (FIG. 4*b*), and testing set (FIG. 4*c*). These datasets are continuous trajectories inscribed in a volume of 8 cm×8 cm×5 cm, which is wider than most typical oral cavities [23], [24] and thus adequate for tongue-tracking applications. The number of magnetic samples collected for the training set is ~403,000, validation is ~305,000, and testing is ~265,000. The validation set follows a similar trajectory to the training set but with a positional shift in each axis to ensure that the model will not overfit the training set. The testing set is a unique trajectory designed to randomly sample the volume, traverse positions unseen in the training and validation sets, and represent curved movement similar to that of the tongue.

Testing for Orientation Compensation. The aforementioned trajectories are all traversed without any rotation since our method does not require the tracer to be rotated to train the neural network. Consequently, an additional testing set was collected to evaluate the accuracy of our localization model with orientation compensation (FIG. 4E). This testing set includes the same 3D positions as the aforementioned testing set but with varying pitch and roll. For both rotations, the angles follow a sinusoidal waveform with a ±50° amplitude but different frequencies to generate many combinations of pitch and roll values. The resulting dataset has the same number of samples as its non-rotated counterpart (~265,000).

Tracking Accuracy of Magnetic Localization. As noted above, in one embodiment, it was empirically observed that the architecture of the neural network that provides the lowest errors included 2 hidden layers, 40 neurons per layer, soft-plus activation function, and RMSprop as the optimizer with 256 batch size and 0.05 learning rate. The positional errors for the datasets used to train and assess the tracking accuracy of our localization model are shown in FIG. 4. FIGS. 4A, 4B, and 4C, respectively, show positional errors of the exemplary magnetic localization operation to train (FIG. 4A) and assess (validation, FIG. 4B; and testing trajectories, FIG. 4C) the tracking accuracy of the exemplary localization operation. FIG. 4D shows a box plot of all errors.

Training Results. In FIG. 4A, the errors observed for the training set have median and Q3 values of 0.76 mm and 1.29 mm, respectively. The validation set (FIG. 4B) has a median error of 0.93 mm and a Q3 error of 1.49 mm. It can be observed that overfitting did not occur (the errors for validation and training sets are similar). In FIG. 4C, the results for the testing set have a median error of 0.83 mm and a Q3 of 1.42 mm. Overall, the results show that 75% of the errors are within 1.5 mm, and virtually all errors are within 3 mm for any position of the tracer in a volume of 8×8×5 cm3.

It was consistently observed across the data set that the tracking accuracy is better in the lower and central parts of the volume with errors below 1 mm. However, the accuracy tends to decrease with increased Z-axis position, which may be explained by the tracer moving further from the magnet strip resulting in a reduced signal-to-noise ratio due to a weaker magnetic field. By adjusting the magnetic strength of the local magnetic field by varying the number, size, and geometric arrangement of the magnets in the strip, a reduction in error may be attained with higher Z values.

Tracking Accuracy with Rotating Tracer. To better demonstrate the performance of the exemplary orientation compensation method in increasing the tracking accuracy, the study evaluated the results against the performance of a system with non-compensated errors. FIGS. 4E and 4F show the positional errors of the testing set, with the tracer being rotated along with its pitch and roll. The errors are shown in FIG. 4E as a heat map of the trajectory and in FIG. 4F as a box plot for the non-compensated (original) errors of FIGS. 4A-4C compared to the orientation-compensated results of FIG. 4E.

When orientation compensation is not used, the positional errors were observed to have a median value of 18.3 mm and a Q3 of 27 mm. When compensating for the tracer's orientation, a significant increase in accuracy is observed with a median error of 2.9 mm and Q3 of 4.2 mm.

The level of accuracy is satisfactory for many motion tracking applications, including tongue tracking for applications not related to speech, such as alternative control for powered wheelchairs [6]. Speech-related applications might require a higher degree of tracking accuracy with [9] reporting that an accuracy of 0.5 mm is considered acceptable for speech. The latest EMA model (AG501, Carstens Medizinelektronik GmbH, Bovenden, Germany) has a reported positional tracking accuracy of 0.3 mm (RMSE) [25]. It is noted that the evaluation methods for the tracking accuracy of EMA, such as in [7]-[9], [25] are significantly different. EMA also are unlikely amenable to a wearable form factor.

Discussion

Motion tracking technologies play a vital role in various applications such as robotics, sports, virtual/augmented reality, and entertainment. Chief among them is the tracking of body motion for medical applications, which, for example, is included as part of assistive technologies to assist in the rehabilitation of physical disabilities, or as an alternative control used by people with quadriplegia. However, tracking the motion of the tongue remains a challenge despite its valuable use in speech rehabilitation [1], [2], as part of a silent speech interface [3]-[5], and as an alternative method of controlling devices [6]. There are many technical difficulties in tracking the motion of the tongue that render most available motion tracking systems unsuitable. For instance, optical-based tracking (i.e., computer vision, reflective markers) cannot be used due to the lack of visibility of the inside of the mouth, and any suitable technology may be minimally obtrusive to avoid impeding the natural tongue motion.

Commercially available tracking technologies such as the Electromagnetic Articulograph (EMA) are well known for tracking with millimetric accuracy the 3D position and 2D orientation of multiple tracers on the tongue [7]-[9]. EMA functions by emitting a strong electromagnetic field that surrounds the user's oral cavity in which coil-like tracer(s) are glued on the tongue [10]. EMA is generally considered the most accurate tongue tracking system currently available, but its use is primarily restricted to speech science research because its limitations include a lack of portability due to the need for large electromagnetic transmitters and a high cost. The Electropalatograph (EPG) detects the points of contact between the tongue and the palate using electrodes embedded in an over-the-palate mouthpiece, enabling a discretized 2D view of the tongue surface [11]. EPG is mainly used in speech therapy [12] because its lack of continuous motion tracking prevents its widespread use since many phonemes are produced without palatal contact. Ultrasound Tongue Imaging (UTI) relies on high-frequency sound waves to generate a 2D image of the sagittal plane of the oral cavity [13]. Although the cross-section of the tongue is captured, the tongue tip is usually not visible on the images due to the hyoid and/or the jaw-bone [14]. Additionally, the ultrasound probe may be needed to be held under the user's jaw, which is not hands-free and can restrict jaw motion during speech.

More recently, there has been a growing body of research on the development of a permanent magnet localization (PML) method to track the motion of a small magnet [15]-[17]. Tongue tracking was achieved by placing the magnet on the tongue [18], [19]. The basic principle of PML relies on capturing the magnetic field generated from the magnet by an array of magnetometers. The changes in the magnetic field due to the motion of the magnet are fed into a localization algorithm that estimates the magnet's position and orientation. PML has the potential to overcome many of the shortcomings of the current tongue tracking technologies since the tracer (i.e., magnet) is small enough to not be obtrusive, provides continuous tracking in the whole 3D space, and is capable of providing millimetric tracking accuracy that is required for typical tongue tracking applications such as speech recognition [10]. However, in its prior design, PML has significant limitations that hinder its practical use for tongue tracking. For instance, its localization algorithm requires input from multiple magnetometers, which may need to be placed close to the mouth to measure the weak magnetic field produced by the small magnet. These magnetometers may need to be fixed in place to provide a stable frame of reference which requires these sensors to be mounted on a headset that can be cumbersome in activities of daily living and subject to social stigma. Using a larger magnet may not be practical as it may impede the natural motion of the tongue. To this end, the distance between the magnet and the magnetometers may be restricted due to the limited strength of the available magnetic field source. Additionally, PML is incapable of tracking multiple magnets since the magnetic field generated by each magnet cannot be uniquely measured or identified.

U.S. Pat. Nos. 8,044,766B2 and 8,242,880B2 each describe a tracking system dedicated to capturing tongue motion, in which a permanent magnet is attached to the tongue, and an array of at least one magnetometer is placed proximal to the magnet. In that system, the permanent magnet is the tracer unit being tracked through its emitted magnetic field.

The exemplary inertial measurement unit (IMU), in some embodiments, is a tongue tracer and the magnetic source (e.g., array of permanent magnets, electromagnets) is external to the tongue. This can have many advantages over the permanent magnet localization (PML) method, including, but not limited to, an increased tracking accuracy by allowing the strength of the local magnetic field to be increased without increasing the size of the tongue tracer, which would have impeded natural tongue motion. Furthermore, the use of a gyroscope and an accelerometer provides added information that is missing in the PML method. This increases tracking accuracy by reducing the complexity of the localization estimation from a 5-dimensional state (3D position+2D orientation) to a 3-dimensional state (position only since orientation is provided by the gyroscope and accelerometer).

Also, the form factor of the system is smaller and more discreet. The prior system defines the use of at least one magnetometer, but in practice, requires anywhere from 4 to 24 magnetometers which lead to a large, obtrusive device. In contrast, the exemplary system and method can operate using only one magnetometer and a magnetic source that can be distanced far enough from the sensor that it can be hidden from view behind clothes or embedded in accessories (e.g., neckband, earpiece, glasses).

Finally, multiple tracers can be tracked simultaneously in the exemplary system since each tracer is a standalone unit.

In some embodiments, the exemplary system can be used for any applications that need, or benefit from, a high degree of accuracy in tracking, allow movements in all dimensions, including those where the line-of-sight is obstructed between the transmitter/source and the receiver/tracer, and need many tracers to be tracked simultaneously. In this addressable market, there are at least two target markets that were identified. Tracking tongue motion is a target application that can be used in real-time speech recognition, as a visualization tool to accelerate the recovery in the treatment of speech disorders, and as an alternate controller for people with physical paralysis to be more autonomous by controlling devices used in their daily life (e.g., driving their wheelchair, make a call from their mobile device, using an internet browser on their computer). A second target application is body motion tracking that is useful in medical applications such as in the evaluation of rehabilitation efficacy in physical therapy for joint articulation and as part of a diagnostic tool to predict health issues that affect motricity. The exemplary system can also be used in the professional sports industry to improve performance, avoid injuries, or assess recovery of normal motricity after an injury.

In tongue tracking applications, the advantages of an exemplary system include its portability and wearability that enable it to be used in activities of daily living, unobtrusiveness, affordability, and simplicity to setup and use. Commercially available tracking technologies such as the Electromagnetic Articulograph (EMA) are well known for tracking with millimetric accuracy the 3D position and 2D orientation of multiple tracers on the tongue. EMA functions by emitting a strong electromagnetic field that surrounds the user's oral cavity in which coil-like tracer(s) are glued on the tongue. EMA is generally considered the most accurate tongue tracking system currently available, but its use is primarily restricted to speech science research because its limitations include a lack of portability due to the need for large electromagnetic transmitters and a high cost. The Electropalatograph (EPG) detects the points of contact between the tongue and the palate using electrodes embedded in an over-the-palate mouthpiece, enabling a discretized 2D view of the tongue surface. EPG is mainly used in speech therapy because of its lack of continuous motion tracking that prevents its widespread use, and its usefulness is limited since many phonemes are produced without palatal contact. Ultrasound Tongue Imaging (UTI) relies on high-frequency sound waves to generate a 2D image of the sagittal plane of the oral cavity. Although the cross-section of the tongue is captured, the tongue tip is usually not visible on the images due to the hyoid and/or the jawbone. Additionally, the ultrasound probe may be needed to be held under the user's jaw, which is not hands-free and can restrict jaw motion during speech.

For body motion tracking, the gold standard is optical tracking, in which a light source is reflected by markers and captured by an array of cameras (e.g., OptiTrack, Vicon). This system provides a high resolution in tracking but requires a line-of-sight between each component of the system: light source to markers and markers to cameras. This limits the type of movements that can be tracked or requires more cameras to increase coverage while each camera is expensive. The exemplary system employs a non-line-of-sight operation, i.e., it can track the motion of a tracer for any movement as long as the tracer remains in the working volume defined by the strength of the locally generated magnetic field.

Alternating (AC) electromagnetic trackers are a new type of motion capture that is being used for body motion tracking (e.g., Polhemus). This is also a non-line-of-sight tracking system that uses alternating electromagnetic fields to perform localization of coil-like receivers in a similar fashion to EMA. The major issue of this technology is its high sensitivity to electromagnetic interferences that are ubiquitous since it is the means of wireless communication in radio, cellular signals, WiFi, Bluetooth, near field communication, among many others. Conversely, the exemplary system is unaffected by AC electromagnetic fields since it relies on a static magnetic field which can be easily attenuated in the exemplary system.

In some embodiments, the exemplary system may be used in combination with any of the devices or systems discussed herein.

In some embodiments, the exemplary system is used for tracking tongue motion to serve the needs of the following target populations: enable people with quadriplegia to be more autonomous, recognize speech in real-time to generate a synthesized voice for people that underwent a laryngectomy, and accelerate the rate of recovery for patients with speech disorders.

Every year, it is estimated that 500,000 people worldwide have accidents that result in severe physical paralysis which has many negative consequences to their overall quality of life, including lower rates of school enrollment or employment and higher financial burden on their household. In the United States, the direct healthcare cost for people living with quadriplegia is estimated at around $1M during the first year and $100 k per subsequent year. Additionally, more than 56% of people with quadriplegia are between the ages of 16-30 years old, and the majority (76%) live in a household with an annual income below $50 k. Therefore, it is imperative for such a population to be more autonomous in order to work and be active members of society. Alternate controllers are used by this population to control devices and even drive their own wheelchair, but they either offer only a limited number of controls (e.g., sip-and-puff) or are not practical to use (e.g., chin joystick). The exemplary system facilitates a tongue tracking system that offers 3D controls, is easy to use, and is affordable.

For people that are unable to produce speech sounds due to the removal of the larynx, silent speech interfaces (SSIs) are a novel assistive technology that can produce synthesized voice by recognizing speech in real-time and from tongue motion alone. Human studies have shown a high level of speech prediction, but, currently, SSIs cannot be used on the side of the lab because tongue tracking is performed by electromagnetic articulographs (EMA), which are not portable. By using the exemplary system instead of EMA, SSIs could be used by the end-users in their daily life. In the United States alone, there is an estimated 13,000 new cases of laryngeal cancers every year for a total of 96,231 in 2017.

There are approximately 5.2 million people with speed disorder, of whom 3.7 million are receiving some form of treatment for the disorder. As a result of more than 70 speech-language pathologists (SLP) that were interviewed across the nation, it was found that most SLPs use rudimentary tools (e.g., tongue depressors) and that visualization of the tongue would improve the outcome of therapy because patients would better perform their speech exercises not only in-office but also at-home. The last point is critical because SLPs complain that patients' adherence to complete at-home speech exercises is usually low, and those who do perform them might reinforce bad articulation since no performance feedback is available to them outside of in-office therapy with their SLP. Thus, SLPs showed great interest in a tongue tracking system because it would track a patient's compliance to complete their exercises and provide objective and meaningful performance feedback to the patient, which would better guide their at-home practice sessions. This has the potential to accelerate the patient's recovery.

Power Wheelchair Control Technology Discussion. There are many alternative controllers that have been developed in the past decades to help power wheelchair users to regain some level of autonomy [1', 2'], with each system typically targeting one modality of control [3']. The head array and sip-and-puff are the most prevalent alternative controllers for people with complete tetraplegia, while chin joysticks are used by some because of their proportional control. Specialized joysticks and switches are limited to persons with some range of motion in their upper body extremities. The head array [4'] provides a few switches that are activated by a press with the head, which can only deliver a simple control and is quickly tiresome for the neck—the sip-and-puff acts as a simple switch by puffing or sipping through a straw [5']. Specialized joysticks offer proportional controls that are bound to the wheelchair [6']. Voice commands are mostly used as a secondary input method to another controller because of a slow information rate, lack of privacy, and inefficiency in a noisy environment [7', 8'].

To efficiently control a complex device, both discrete and proportional controls are needed, such as a keyboard (discrete) and a mouse (proportional) for a computer or a finger tap (discrete) and finger swipe (proportional) for a touchscreen. However, most of the existing alternative controllers are incapable of offering both discrete and proportional inputs, while the others are unable to offer them simultaneously. As a result, this user population is limited to ineffective methods of interacting with devices, particularly those that require complex control schemes. Furthermore, most power wheelchair users would prefer wearable input controls [9'] while most of these controllers are bound to the wheelchair and thus become inaccessible once the users are transferred to a bed, a couch, or any location away from the wheelchair.

There is a growing body of research that attempts to develop advanced alternative controllers based on new sensing technologies and signal processing. For instance, voluntary facial muscle movements can be captured by electromyograms (EMG, FIG. 1) [10', 11'], eye movements by electrooculogram (EOG) [12', 13', 14'], or even a combination of both [15']. The main issue with EOG and EMG is that the recorded electrical signal level is much smaller than the types of interferences and artifacts that are typically present, thus are easily corrupted. Consequently, their setup requires the caregiver to be highly trained to place the electrodes precisely while also applying conductive gel carefully at the skin-electrode contact to obtain sufficient signal quality. These issues alone reduce the practicality of these systems since not all caregivers can be trained to perform such setup properly. Also, as explained in [14'], the high degree of concentration required by the users of EOG increases tiredness and leads to progressive difficulty to use eye movements to issue desired commands.

Eye gaze can be detected by specialized cameras [16', 17', 18'] and used to drive wheelchairs by activating commands depending on where the user's gaze is dwelling on a screen. The main issue with eye gaze trackers is that the cameras are sensitive to the lighting environment, particularly when used outdoors because the infrared light wavelengths interfere with gaze detection. Also, users expressed difficulties with the "Midas Touch" problem in which unintended commands are issued when searching for the next command on the screen [18']. Increasing dwell time to reduce errors results in a slower input rate and increased fatigue due to a higher concentration required for each command. But mostly, using eye gaze for command activation is unnatural [18'], though it might be the only remaining motion for individuals at a high progressed stage of neurodegenerative disease.

The brain-computer interface (BCI) [19', 20', 21'] is a promising breakthrough technology that records brain signals to control devices. In the current research, over-the-scalp electroencephalography (EEG) is used instead of intracranial recording to avoid surgeries that are highly invasive, risky, and costly. Regardless of the recording hardware, complex training and signal processing are required to classify commands from the multi-channel recordings of brain activity [20']. In general, the algorithms require extensive training that would be impractical in the real world, and the need for high computer processing resources would be expensive and power-hungry. Another prominent issue with BCI is that the placement of the electrodes is not trivial and requires proper skin-to-electrode contact to preserve the already small signals recorded by external EEG. This necessitates the use of conductive gel and specialized adhesives, which drastically impact the usability of BCIs through increased cost, impracticality, and discomfort. Intracranial recording probes might solve some of the signal quality issues with over-the-scalp EEG, but they are invasive and create other problems such as brain tissue damage due to abrasion and the need for high-risk brain surgeries. New companies like Neuralink are attempting to develop safer methods for implantation but are still at the early research phase.

Head tracking is becoming the favorite contender among the new generation of alternative controllers, with commercial products being developed by new technology companies. Inertial sensors composed of gyroscopes and accelerometers are typically used to track the head orientation that is then translated into proportional control [19', 20', 21']. The advantages of head trackers include inexpensive inertial sensors that are mass-produced for consumer electronics, the outputs are proportional and thus can emulate a joystick, and the neck does not fatigue as easily as the eye. However, the range of motion of the neck can be severely limited for some individuals [22', 23'], which reduces the effectiveness of head tracking. Though, their main issue is they only offer a single modality of control and therefore must rely on other controllers to issue discrete commands that are needed for the full control of a wheelchair.

To overcome the lack of discrete controls, the capabilities of head trackers could be augmented with tongue control that is a new approach that has gained ground in research in the past decade. The tongue has many advantages over other head/face modalities because it is less prone to fatigue, moves in three dimensions can be precisely controlled when not affected by a neurodegenerative disease, and can be hidden from view. However, tracking the tongue is challenging because intra-oral parts must be coated with biocompatible and waterproof materials that should also be durable, flexible, and small enough to not hinder natural tongue motion. Tongue control systems can use inductive coils [24'], infrared proximity sensors [25'], permanent magnets [26', 27', 28'], or simply by pressure on force-sensing resistors [29', 30']. Most of these tongue tracking systems rely on a palatal overcast that is obtrusive and hinders natural speech due to the reshaping of the oral cavity. Since a practical version of these systems must be wireless, these issues will only be exacerbated by the added volume needed for a battery, controller, antenna, and supporting electronic components. In magnet-based tracking, an array of magnetometers must be placed next to the mouth, which makes the system highly conspicuous.

Example Computing System

It should be appreciated that the logical operations described above and in the appendix can be implemented (1) as a sequence of computer-implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as state operations, acts, or modules. These operations, acts, and/or modules can be implemented in software, in firmware, in special purpose digital logic, in hardware, and any combination thereof. It should also be appreciated that more or fewer operations can be performed than shown in the figures and described herein. These operations can also be performed in a different order than those described herein.

The computer system is capable of executing the software components described herein for the exemplary method or systems. In an embodiment, the computing device may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 200 to provide the functionality of a number of servers that are not directly bound to the number of computers in the computing device. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or can be hired on an as-needed basis from a third-party provider. Some cloud computing environments may comprise cloud computing resources owned and operated by the enterprise as well as cloud computing resources hired and/or leased from a third-party provider.

In its most basic configuration, a computing device includes at least one processing unit and system memory. Depending on the exact configuration and type of computing device, system memory may be volatile (such as random-access memory (RAM)), non-volatile (such as read-only memory (ROM), flash memory, etc.), or some combination of the two.

The processing unit may be a standard programmable processor that performs arithmetic and logic operations necessary for the operation of the computing device. While only one processing unit is shown, multiple processors may be present. As used herein, processing unit and processor refers to a physical hardware device that executes encoded instructions for performing functions on inputs and creating outputs, including, for example, but not limited to, microprocessors (MCUs), microcontrollers, graphical processing units (GPUs), and application-specific circuits (ASICs). Thus, while instructions may be discussed as executed by a processor, the instructions may be executed simultaneously, serially, or otherwise executed by one or multiple processors. The computing device may also include a bus or other communication mechanism for communicating information among various components of the computing device.

Computing devices may have additional features/functionality. For example, the computing device may include additional storage such as removable storage and non-removable storage including, but not limited to, magnetic or optical disks or tapes. Computing devices may also contain network connection(s) that allow the device to communicate with other devices, such as over the communication pathways described herein. The network connection(s) may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing devices may also have input device(s) such as keyboards, keypads, switches, dials, mice, trackballs, touch screens, voice recognizers, card readers, paper tape readers, or other well-known input devices. Output device(s) such as printers, video monitors, liquid crystal displays (LCDs), touch screen displays, displays, speakers, etc., may also be included. The additional devices may be connected to the bus in order to facilitate the communication of data among the components of the computing device. All these devices are well known in the art and need not be discussed at length here.

The processing unit may be configured to execute program code encoded in tangible, computer-readable media.

Tangible, computer-readable media refers to any media that is capable of providing data that causes the computing device (i.e., a machine) to operate in a particular fashion. Various computer-readable media may be utilized to provide instructions to the processing unit for execution. Example tangible, computer-readable media may include but is not limited to volatile media, non-volatile media, removable media, and non-removable media implemented in any method or technology for storage of information such as computer-readable instructions, data structures, program modules, or other data. System memory 230, removable storage, and non-removable storage are all examples of tangible computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In light of the above, it should be appreciated that many types of physical transformations take place in the computer architecture in order to store and execute the software components presented herein. It also should be appreciated that the computer architecture may include other types of computing devices, including hand-held computers, embedded computer systems, personal digital assistants, and other types of computing devices known to those skilled in the art.

In an example implementation, the processing unit may execute program code stored in the system memory. For example, the bus may carry data to the system memory 230, from which the processing unit receives and executes instructions. The data received by the system memory may optionally be stored on the removable storage or the non-removable storage before or after execution by the processing unit.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language, and it may be combined with hardware implementations.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "5 approximately" one particular value and/or to "about" or "approximately" another particular value. When such a range is expressed, other exemplary embodiments include from the one particular value and/or to the other particular value.

By "comprising" or "containing" or "including" is meant that at least the name compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5).

Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The following patents, applications, and publications as listed below and throughout this document are hereby incorporated by reference in their entirety herein.

[1] W. F. Katz and M. R. McNeil, "Studies of articulatory feedback treatment for apraxia of speech based on electromagnetic articulography," Perspectives on Neurophysiology and Neurogenic Speech and Language Disorders, vol. 20, no. 3, pp. 73-80, 2010.

[2] W. Katz, T. F. Campbell, J. Wang, E. Farrar, J. C. Eubanks, A. Balasubramanian, B. Prabhakaran, and R. Rennaker, "Opti-speech: A real-time, 3d visual feedback system for speech training," in Proc. Interspeech, 2014, pp. 1174-1178.

[3] M. Kim, B. Cao, T. Mau, and J. Wang, "Speaker-independent silent speech recognition from flesh-point articulatory movements using a lstm neural network," IEEE/ACM Transactions on Audio, Speech, and Language Processing, vol. 25, no. 12, pp. 2323-2336, 2017.

[4] B. Denby, T. Schultz, K. Honda, T. Hueber, J. M. Gilbert, and J. S. Brumberg, "Silent speech interfaces," Speech Communication, vol. 52, no. 4, pp. 270-287, 2010.

[5] T. Schultz, M. Wand, T. Hueber, D. J. Krusienski, C. Herff, and J. S. Brumberg, "Biosignal-based spoken communication: A survey," IEEE/ACM Transactions on Audio, Speech, and Language Processing, vol. 25, no. 12, pp. 2257-2271, 2017.

[6] M. N. Sahadat, N. Sebkhi, D. Anderson, and M. Ghovanloo, "Optimization of tongue gesture processing algorithm for standalone multimodal tongue drive system," IEEE Sensors J., vol. 19, no. 7, pp. 2704-2712, 2019.

[7] Y. Yunusova, J. R. Green, and A. Mefferd, "Accuracy assessment for ag500, electromagnetic articulograph," Journal of Speech, Language, and Hearing Research, vol. 52, no. 2, pp. 547-555, 2009.

[8] J. J. Berry, "Accuracy of the ndi wave speech research system," Journal of Speech, Language & Hearing Research, vol. 54, no. 5, pp. 1295-1301, 2011.

[9] C. Savariaux, P. Badin, A. Samson, and S. Gerber, "A comparative study of the precision of carstens and northern digital instruments electromagnetic articulographs," Journal of Speech, Language, and Hearing Research, vol. 60, no. 2, pp. 322-340, 2017.

[10] J. Wang, A. Samal, P. Rong, and J. R. Green, "An optimal set of flesh points on tongue and lips for speech-movement classification," Journal of Speech, Language, and Hearing Research, vol. 59, no. 1, pp. 15-26, February 2016.

[11] S. Kelly, A. Main, G. Manley, and C. McLean, "Electropalatography and the linguagraph system," Medical Engineering & Physics, vol. 22, no. 1, pp. 47-58, 2000.

[12] F. Gibbon and A. Lee, "Electropalatography for older children and adults with residual speech errors," Semin Speech Lang, vol. 36, no. 04, pp. 271-282, 2015.

[13] L. M'enard, J. Aubin, M. Thibeault, and G. Richard, "Measuring tongue shapes and positions with ultrasound imaging: A validation experiment using an articulatory model," Folia Phoniatrica et Logopaedica, vol. 64, no. 2, pp. 64-72, 2012.

[14] M. Grimaldi, B. Gili Fivela, F. Sigona, M. Tavella, P. Fitzpatrick, L. Craighero, L. Fadiga, G. Sandini, and G. Metta, "New technologies for simultaneous acquisition of speech articulatory data: 3d articulograph, ultrasound and electroglottograph," Proceedings of LangTech, pp. 1-5, 2008.

[15] C. Hu, M. Li, S. Song, R. Zhang, and M. Q.-H. Meng, "A cubic 3-axis magnetic sensor array for wirelessly tracking magnet position and orientation," IEEE Sensors J., vol. 10, no. 5, pp. 903-913, 2010.

[16] S. Song, B. Li, W. Qiao, C. Hu, H. Ren, H. Yu, Q. Zhang, M. Q.-H. Meng, and G. Xu, "6-d magnetic localization and orientation method for an annular magnet based on a closed-form analytical model," IEEE Trans. Magn., vol. 50, no. 9, pp. 1-11, 2014.

[17] S. Foong and Z. Sun, "High accuracy passive magnetic field-based localization for feedback control using principal component analysis," MDPI Sensors, vol. 16, no. 8, p. 1280, 2016.

[18] N. Sebkhi, D. Desai, M. Islam, J. Lu, K. Wilson, and M. Ghovanloo, "Multimodal speech capture system for speech rehabilitation and learning," IEEE Trans. Biomed. Eng., vol. 64, no. 11, pp. 2639-2649, 2017.

[19] N. Sebkhi, N. Sahadat, S. Hersek, A. Bhavsar, S. Siahpoushan, M. Ghoovanloo, and O. T. Inan, "A deep neural network-based permanent magnet localization for tongue tracking," IEEE Sensors J., vol. 19, no. 20, pp. 9324-9331, 2019.

[20] C. Lv, X. Chen, H. Huang, and Z. Zhou, "Study on calibration method for tri-axial accelerometers," in 2015 IEEE Metrology for Aerospace (MetroAeroSpace), June 2015, pp. 15-20.

[21] X. Cui, Y. Li, Q. Wang, M. Zhang, and J. Li, "Three-axis magnetometer calibration based on optimal ellipsoidal fitting under constraint condition for pedestrian positioning system using foot-mounted inertial sensor/magnetometer," in 2018 IEEE/ION Position, Location and Navigation Symposium (PLANS), April 2018, pp. 166-174.

[22] P. Livermore, C. Finlay, and M. Bayliff, "Recent north magnetic pole acceleration towards siberia caused by flux lobe elongation," Nature Geoscience, vol. 13, no. 5, p. 387-391, May 2020.

[23] K. Rudy and Y. Yunusova, "The effect of anatomic factors on tongue position variability during consonants," Journal of Speech, Language, and Hearing Research, vol. 56, no. 1, pp. 137-149, February 2013.

[24] Y. Yunusova, J. S. Rosenthal, K. Rudy, M. Baljko, and J. Daskalogiannakis, "Positional targets for lingual consonants defined using electromagnetic articulography," Journal of the Acoustical Society of America, vol. 132, no. 2, pp. 1027-1038, 2012.

[25] F. Sigona, M. Stella, A. Stella, P. Bernardini, B. Gili Fivela, and M. Grimaldi, "Assessing the position tracking reliability of carstens' ag500 and ag501 electromagnetic articulographs during constrained movements and speech tasks," Speech Communication, vol. 104, pp. 1-35, 2018.

[1'] S. Evans, C. Neophytou, L. de Souza, and A. O. Frank, "Young people's experiences using electric powered indoor—outdoor wheelchairs (EPIOCs): potential for enhancing users' development?," Disabil Rehabil, vol. 29, no. 16, pp. 1281-94, Aug. 30, 2007.

[2'] R. C. Simpson, E. F. LoPresti, and R. A. Cooper, "How many people would benefit from a smart wheelchair?," J Rehabil Res Dev, vol. 45, no. 1, pp. 53-71, 2008.

[3'] L. Watanabe, "A hierarchy of driving controls, Where to Start & How to Proceed When Assessing Power Chair Options," Mobility Management, June, 2021. [Online]. Available: https://mobilitymgmt.com/Articles/2017/10/01/Driving-Controls.aspx.

[4'] Stealth Products, "i-drive head arrays," [Online]. Available: https://stealthproducts.com/about/idrive-head-arrays.

[5'] I. Mougharbel, R. El-Hajj, H. Ghamlouch, and E. Monacelli, "Comparative study on different adaptation approaches concerning a sip and puff controller for a powered wheelchair," in IEEE Science and Information Conference, 2013, pp. 597-603.

[6'] B. E. Dicianno, R. A. Cooper, and J. Coltellaro, "Joystick control for powered mobility: current state of technology and future directions," Phys Med Rehabil Clin N Am, vol. 21, no. 1, pp. 79-86, February, 2010.

[7'] R. Chauhan, Y. Jain, H. Agarwal, and A. Patil, “Study of Implementation of Voice Controlled Wheelchair,” International Conf. on Advanced Computing and Communication Systems, 2016.

[8'] A. Skraba, A. Koloivari, D. Kofjac, and R. Stojanović, “Prototype of Speech Controlled Cloud Based Wheelchair Platform for Disabled Persons” in IEEE Mediterranean Conference on Embedded Computing, 2014, pp. 162-165.

[9'] P. Carrington, A. Hurst, and S. K. Kane, “Wearables and chairables: Inclusive design of mobile input and output techniques for power wheelchair users,” in Proc. of the SIGCHI Conf. on Human Factors in Computing Systems, 2014, pp. 3103-3112.

[10'] E. Scheme, K. Biron, and K. Englehart, “Improving Myoelectric Pattern Recognition Positional Robustness Using Advanced Training Protocols,” IEEE Engineering in Medicine and Biology Society, pp. 4828-4831, 2011.

[11'] E. Scheme, and K. Englehart, “Electromyogram pattern recognition for control of powered upper-limb prostheses: State of the art and challenges for clinical use,” Journal of Rehabilitation Research and Development, vol. 48, no. 6, pp. 643-659, 2011.

[12'] B. Champaty, J. Jose, K. Pal, and A. Thirugnanam, “Development of EOG Based Human Machine Interface control System for Motorized Wheelchair,” International Conf. on Emerging Research Areas: Magnetics, Machines and Drives, 2014.

[13'] E. Ianez, J. M. Azorin, and C. Perez-Vidal, “Using Eye Movement to Control a Computer: A Design for a Lightweight Electro-Oculogram Electrode Array and Computer Interface,” PLOS One, vol. 8, no. 7, Jul. 3, 2013.

[14'] R. Barea Navarro, L. Boquete Vázquez, and E. López Guillén, “EOG-based wheelchair control,” Smart Wheelchairs and Brain-Computer Interfaces, pp. 381-403: Academic Press, 2018.

[15'] N. M. Lopez, E. Orosco, E. Perez, S. Bajinay, R. Zanetti, and M. E. Valentinuzzi, “Hybrid Human-Machine Interface to Mouse Control for Severely Disabled People,” International Journal of Engineering and Innovative Technology, vol. 4, no. 11, pp. 164-171, 2015.

[16'] A. Bulling, and H. Gellersen, “Toward Mobile Eye-Based Human-Computer Interaction,” IEEE Pervasive Computing, vol. 9, no. 4, pp. 8-12, October-December, 2010.

[17'] A. Krolak, and P. Strumillo, “Eye-blink detection system for human-computer interaction,” Universal Access in the Information Society, vol. 11, no. 4, pp. 409-419, 2012.

[18'] J. P. Hansen, K. Tsrning, A. S. Johansen, K. Itoh, and H. Aoki, “Gaze typing compared with input by head and hand,” in Proceedings of the 2004 symposium on Eye tracking research & applications, 2004, pp. 131-138.

[19'] J. Y. Long, Y. Q. Li, H. T. Wang, T. Y. Yu, J. H. Pan, and F. Li, “A Hybrid Brain Computer Interface to Control the Direction and Speed of a Simulated or Real Wheelchair,” IEEE Trans. on Neural Systems and Rehabilitation Engineering, vol. 20, no. 5, pp. 720-729, September, 2012.

[20'] A. Fernandez-Rodriguez, F. Velasco-Alvarez, and R. Ron-Angevin, “Review of real brain-controlled wheelchairs,” J Neural Eng, vol. 13, no. 6, pp. 061001, December, 2016.

[21'] A. C. Lopes, G. Pires, and U. Nunes, “Assisted navigation for a brain-actuated intelligent wheelchair,” Robotics and Autonomous Systems, vol. 61, no. 3, pp. 245-258, 2013.

[22'] A. E. Ropper, M. T. Neal, and N. Theodore, “Acute management of traumatic cervical spinal cord injury,” Practical neurology, vol. 15, no. 4, pp. 266-272, 2015.

[23'] M. Paralyzed Veterans of America Consortium for Spinal Cord, “Preservation of upper limb function following spinal cord injury: a clinical practice guideline for health-care professionals,” The journal of spinal cord medicine, vol. 28, no. 5, pp. 434-470, 2005.

[24'] M. Mohammadi, H. Knoche, and L. N. S. Andreasen Struijk, “Continuous tongue robot mapping for paralyzed individuals improves the functional performance of tongue-based robotic assistance,” IEEE Trans. Biomed Engineering, vol. PP, Jan. 29, 2021.

[25'] T. S. Saponas, D. Kelly, B. A. Parviz, and D. S. Tan, “Optically Sensing Tongue Gestures for Computer Input,” ACM Symposium on User Interface Software and Technology, pp. 177-180, 2009.

[26'] N. Sebkhi, D. Desai, M. Islam, J. Lu, K. Wilson, and M. Ghovanloo, “Multimodal Speech Capture System for Speech Rehabilitation and Learning,” IEEE Trans. Biomedical Engineering, vol. 64, no. 11, pp. 2639-2649, November, 2017.

[27'] M. N. Sahadat, N. Sebkhi, D. Anderson, and M. Ghovanloo, “Optimization of Tongue Gesture Processing Algorithm for Standalone Multimodal Tongue Drive System,” IEEE Sensors Journal, vol. 19, no. 7, pp. 2704-2712, 2019.

[28'] N. Sebkhi, N. Sahadat, S. Hersek, A. Bhavsar, S. Siahpoushan, M. Ghoovanloo, and O. T. Inan, “A Deep Neural Network-Based Permanent Magnet Localization for Tongue Tracking,” IEEE Sensors Journal, vol. 19, no. 20, pp. 9324-9331, 2019.

[29'] Brandon Dang, Brij Purohit, Dharav Sarang, and K. George, “Tongue driven wireless electronic communication device,” in IEEE Sensors Applications Symposium, 2017, pp. 1-5.

[30'] A. Velasquez-Lopez, D. Velasquez-Rendon, J. S. Amaya-Quiroz, L. D. Jimenez-Franco, and H. Trefftz, “Development of a Tongue Machine Interface for Quadriplegic Patients,” Proceedings of the 21st International Conference on Engineering Design, pp. 449-458, 2017.

[31'] M. W. Abdullah, X. Fafoutis, E. Mellios, M. Klemm, and G. S. Hilton, “Investigation into off-body links for wrist mounted antennas in bluetooth systems.” pp. 1-5.

[32'] K. Shinohara, and J. O. Wobbrock, “In the shadow of misperception: assistive technology use and social interactions,” in Proceedings of the SIGCHI Conf. on Human Factors in Computing Systems, 2011, pp. 705-714.

[33'] N. Sebkhi, A. Bhavsar, D. V. Anderson, J. Wang, and O. T. Inan, “Inertial Measurements for Tongue Motion Tracking Based on Magnetic Localization with Orientation Compensation,” IEEE Sensors Journal, vol. 21, no. 6, pp. 7964-7971, 2021.

[34'] A. Laumann, J. Holbrook, J. Minocha, D. Rowles, B. Nardone, D. West, J. Kim, J. Bruce, E. J. Roth, and M. Ghovanloo, “Safety and efficacy of medically performed tongue piercing in people with tetraplegia for use with tongue-operated assistive technology,” Top Spinal Cord Inj Rehabil, vol. 21, no. 1, pp. 61-76, 2015.

[35'] S. Mabrouk, D. Whittingslow, and O. T. Inan, “Robust Method for Mid-Activity Tracking and Evaluation of Ankle Health Post-Injury,” IEEE Trans Biomed Eng, vol. 68, no. 4, pp. 1341-1350, April, 2021.

[36'] V. G. Ganti, A. M. Carek, B. N. Nevius, J. A. Heller, M. Etemadi, and O. T. Inan, “Wearable Cuff-Less Blood Pressure Estimation at Home via Pulse Transit Time,”

IEEE Journal of Biomedical and Health Informatics, vol. 25, no. 6, pp. 1926-1937, 2021.

[37'] B. Semiz, A. M. Carek, J. C. Johnson, S. Ahmad, J. A. Heller, F. G. Vicente, S. Caron, C. W. Hogue, M. Etemadi, and O. T. Inan, "Non-Invasive Wearable Patch Utilizing Seismocardiography for Peri-Operative Use in Surgical Patients," IEEE Journal of Biomedical and Health Informatics, vol. 25, no. 5, pp. 1572-1582, 2021.

[38'] M. N. Sahadat, A. Alreja, and M. Ghovanloo, "Simultaneous multimodal PC access for people with disabilities by integrating head tracking, speech recognition, and tongue motion," IEEE Trans. on Biomedical Circuits and Systems, vol. 12, no. 1, pp. 192-201, 2018.

[39'] J. Kim, H. Park, J. Bruce, D. Rowles, J. Holbrook, B. Nardone, D. P. West, A. E. Laumann, E. Roth, E. Veledar, and M. Ghovanloo, "Qualitative assessment of tongue drive system by people with high-level spinal cord injury," J Rehabil Res Dev, vol. 51, no. 3, pp. 451-65, 2014.

[40'] L. Keeler, R. L. Kirby, K. Parker, K. D. McLean, and J. A. Hayden, "Effectiveness of the Wheelchair Skills Training Program: a systematic review and meta-analysis," Disabil Rehabil Assist Technol, vol. 14, no. 4, pp. 391-409, May, 2019.

[41'] D. Dawson, R. Chan, and E. Kaiserman, "Development of the Power-Mobility Indoor Driving Assessment for Residents of Long-Term Care Facilities: A Preliminary Report," Canadian Journal of Occupational Therapy, vol. 61, no. 5, pp. 269-276, 1994.

What is claimed is:

1. A method for tracking motion of a body part, the method comprising:

receiving a set of one or more motion-associated signals from one or more wearable sensors disposed on the body part, wherein the one or more wearable sensors include a first wearable sensor that is one of an accelerometer, a motion sensor, a position sensor, or an inertial measurement sensor;

receiving a set of one or more magnetic measurement associated signals from one or more magnetic sensors disposed on the body part, wherein the one or more magnetic sensors are fixed in relation to the first wearable sensor, and wherein the one or more magnetic sensors are placed in proximity to one or more local magnetic field sources disposed on the body; and determining, by a processor, a localization-associated measurement value using the magnetic measurement associated signals and the one or more motion-associated signals, wherein the localization-associated measurement value is determined from the magnetic measurement associated signals adjusted by the one or more motion-associated signals.

2. The method of claim 1, further comprising:

determining, by the processor, a motion-associated measurement value, wherein the motion-associated measurement value has been determined from the motion-associated signals and adjusted for measurement drift based on the localization-associated measurement value.

3. The method of claim 1, wherein the one or more wearable sensors further include a second wearable sensor that is one of the motion sensor, the position sensor, the inertial measurement sensor, or a gyroscope-based sensor, wherein the second wearable sensor is a different type from the first wearable sensor.

4. The method of claim 2, wherein the adjustment for the measurement drift based on the one or more magnetic measurement associated signals includes compensation for magnetic localization.

5. The method of claim 1, wherein the magnetic measurement associated signals is adjusted by orientation or angle estimations derived from an accelerometer and/or gyroscopic reading.

6. The method of claim 1, wherein the localization-associated measurement value comprises a first position value, a second position value, and a third position value.

7. The method of claim 2, wherein the motion-associated measurement value is adjusted by the localization-associated measurement value via a weighted average operation over time or via a dynamic averaging operation.

8. The method of claim 1, wherein the localization-associated measurement value is determined using a trained neural network.

9. The method of claim 8, wherein the neural network is trained using magnetic measurement associated signals acquired by a test rig configured to provide one or more axis position data and one or more orientation data.

10. The method of claim 1, wherein the localization-associated measurement value is determined using a trained machine learning algorithm or a transfer function derived from dynamic system analysis.

11. The method of claim 10, wherein the machine learning algorithm is trained using magnetic measurement associated signals acquired by a test rig configured to provide one or more position data and one or more orientation data.

12. The method of claim 2, further comprising:

outputting a motor control signal or command to a wheelchair using the motion-associated measurement value in a human-machine interface operation.

13. The method of claim 1, wherein the localization-associated measurement value and/or the motion-associated measurement value is used: (i) in a human-machine interface operation to direct robotic control or motion control based on sensed location or motion of a tongue, face, lip, head (ii) in a human-machine interface operation for a computer application, (iii) to track motion of the body part for speech therapy assessment or treatment, or (iv) in a human-machine interface operation to direct robotic control or motion control based on sensed location or motion of joint articulation.

14. The method of claim 1, wherein the one or more local magnetic field sources are disposed in a collar located at a neck; in a cap, headband, or skin patch located at a back of an ear; in a cap, headband, or skin patch over a head; in eyewear; or behind teeth or on retainers inside a mouth.

15. A system comprising:

a plurality of wearable sensors, including a first wearable sensor that is one of a motion sensor, a position sensor, or an inertial measurement sensor;

one or more local magnetic field sources to operate with one or more magnetic sensors;

the one or more magnetic sensors, wherein the one or more magnetic sensors are fixed in relation to the first wearable sensor, and wherein the one or more magnetic sensors is placed in proximity to the one or more local magnetic field source; and a processing unit coupled to the plurality of wearable sensors through one or more sensor interface circuitries configured to convert signals received from the plurality of wearable sensors to motion-associated measurement values, the processing unit comprising a processor and memory, the memory having instructions stored thereon, wherein the instructions when executed by the processor causes the processor to:

receive a set of one or more motion-associated signals from the one or more wearable sensors;

receive a set of one or more magnetic measurement associated signals from the one or more magnetic sensors; and determine a localization-associated measurement value using the magnetic measurement associated signals and the one or more motion-associated signals, wherein the localization-associated measurement value is determined from the magnetic measurement associated signals adjusted by the one or more motion-associated signals.

16. The system of claim 15, further comprising:

a housing configured as eyewear, a neck collar, a cap, a headband, a skin patch, or an earpiece, wherein the housing includes a compartment for the processing unit.

17. The system of claim 15, further comprising:

a second set of wearable sensors configured to be mounted at a second body location, wherein the second set of wearable sensors are configured to output one or more reference signals, and wherein the one or more reference signals are used to adjust measurements of the localization-associated measurement value or a motion-associated measurement value determined at a second body position.

18. The system of claim 15, wherein at least one of the plurality of wearable sensors and at least one of the one or more magnetic sensors are co-located on a substrate configured to be positioned on a portion of a tongue.

19. A non-transitory computer-readable medium having instructions stored thereon, wherein the instructions, when executed by a processor, cause the processor to:

receive a set of one or more motion-associated signals from one or more wearable sensors disposed on a body part, wherein the one or more wearable sensors include a first wearable sensor that is one of an accelerometer, a motion sensor, a position sensor, or an inertial measurement sensor;

receive a set of one or more magnetic measurement associated signals from one or more magnetic sensors disposed on the body part, wherein the one or more magnetic sensors are fixed in relation to the first wearable sensor, and wherein the one or more magnetic sensors are placed in proximity to one or more local magnetic field sources disposed on the body; and determine a localization-associated measurement value using the magnetic measurement associated signals and the one or more motion-associated signals, wherein the localization-associated measurement value is been determined from the magnetic measurement associated signals adjusted by the one or more motion-associated signals.

20. The non-transitory computer-readable medium of claim 19, wherein the instructions when executed by the processor, cause the processor to further:

determine a motion-associated measurement value, wherein the motion-associated measurement value has been determined from the motion-associated signals and adjusted for measurement drift based on the localization-associated measurement value.

21. The method of claim 1, wherein second motion-associated signals and magnetic measurement data from at least another sensor disposed on a second body part is used to normalize magnetic field data for the one or more wearable sensors.

22. The method of claim 1, further comprising:

continuously determining, based, at least in part, on the determined localization-associated measurement value, a three-dimensional position and two-dimensional orientation of at least one of the wearable sensors.

* * * * *